(12) United States Patent
Valdez et al.

(10) Patent No.: US 8,394,351 B2
(45) Date of Patent: Mar. 12, 2013

(54) SYNTHESIS OF TRIAZOLE-BASED AND IMIDAZOLE-BASED ZINC CATALYSTS

(75) Inventors: Carlos A. Valdez, San Ramon, CA (US); Joe H. Satcher, Jr., Patterson, CA (US); Roger D. Aines, Livermore, CA (US); Sarah E. Baker, Pleasanton, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 304 days.

(21) Appl. No.: 12/787,356

(22) Filed: May 25, 2010

(65) Prior Publication Data

US 2011/0293496 A1  Dec. 1, 2011

(51) Int. Cl.
*B01D 53/00* (2006.01)
*C07F 15/00* (2006.01)
*C07D 403/00* (2006.01)

(52) U.S. Cl. .................. 423/226; 548/101; 548/255

(58) Field of Classification Search .................. 548/101, 548/255; 423/226
See application file for complete search history.

(56) References Cited

PUBLICATIONS

Touaibia et al., Chemical Communications, pp. 380-382 (2007).*
Feldman et al., "One-Pot Synthesis of 1,4-Disubstituted 1,2,3-Triazoles from in Situ Generated Azides", © 2004 American Chemical Society, Organic Letters 2004, vol. 6, No. 22, p. 3897-3899.
Tamanini et al., "A Synthetically Simple, Click-Generated Cyclam-Based Zinc(II) Sensor", © 2009 American Chemical Society, Inorganic Chemistry 2009, vol. 48, p. 319-324.
Hong et al., "Electrochemically Protected Copper(1)-Catalyzed Azide-Alkyne Cycloaddition", © 2008 Wiley-VCH Verlag GmbH & Co., ChemBioChem 2008, vol. 9, p. 1481-1486.
Chan et al., "Polytriazoles as Copper(1)-Stabilizing Ligands in Catalysis" © 2004 American Chemical Society, Organic Letters 2004, vol. 6, No. 17, p. 2853-2855.
Rostovtsev et al., "A Stepwise Huisgen Cycloaddition Process: Copper(1)-Catalyzed Regioselective "Litigation" of Azides and Terminal Alkynes" Angewandte Chemie—International Edition English 2002, vol. 41, No. 14, p. 2708-2711.
Tornoe et al., "Peptidotriazoles on Solid Phase: [1,2,3]-Triazoles by Regiospecific Copper(I)-Catalyzed 1,3-Dipolar Cycloadditions of Terminal Alkynes to Azides" © 2002 American Chemical Society, Journal of Organic Chemistry 2002, vol. 67, p. 3057-3064.
Kolb et al., "Click Chemistry Diverse Chemical Function from a few good reactions", Angewandte Chemie—International Edition English., vol. 40, p. 2004-2021, (2001).
Nakata et al., "Kinetic study of catalytic $CO_2$ hydration by water-soluble model compound of carbonic anhydrase and anion inhibition effect on $CO_2$ hydration" © 2002 Elsevier Science Inc., Journal of Inorganic Biochemistry, vol. 89, p. 255-266.

(Continued)

*Primary Examiner* — Porfirio Nazario Gonzalez
(74) *Attorney, Agent, or Firm* — Dominic M. Kotab

(57) ABSTRACT

Various methods and structures of complexes and molecules are described herein related to a zinc-centered catalyst for removing carbon dioxide from atmospheric or aqueous environments. According to one embodiment, a method for creating a tris(triazolyl)pentaerythritol molecule includes contacting a pentaerythritol molecule with a propargyl halide molecule to create a trialkyne molecule, and contacting the trialkyne molecule with an azide molecule to create the tris (triazolyl)pentaerythritol molecule. In another embodiment, a method for creating a tris(imidazolyl)pentaerythritol molecule includes alkylating an imidazole 2-carbaldehyde molecule to create a monoalkylated aldehyde molecule, reducing the monoalkylated aldehyde molecule to create an alcohol molecule, converting the alcohol molecule to create an alkyl halide molecule using thionyl halide, and reacting the alkyl halide molecule with a pentaerythritol molecule to create a tris(imidazolyl)pentaerythritol molecule. In another embodiment, zinc is bound to the tris(triazolyl)pentaerythritol molecule to create a zinc-centered tris(triazolyl)pentaerythritol catalyst for removing carbon dioxide from atmospheric or aqueous environments.

27 Claims, 13 Drawing Sheets

PUBLICATIONS

Kimura et al., "Advances in Zinc Models by Small, Mononuclear Zinc (II) Complexes", Metal Sites in Proteins and Models, vol. 89, p. 1-28, (1997).

Zhang et al., A Functional Model for Carbonic Anhydrase: Thermodynamic and Kinetic Study of a Tetraazacyclododecane Complex of Zinc (II) © 1995 American Chemical Society, Inorganic Chemistry 1995, vol. 34, p. 5606-5614.

Zhang et al., "Kinetics and Mechanism of the Hydration of $CO_2$ and Dehydration of $HCO_3$-Catalyzed in a Zn(II) Complex of 1,5,9-Triazacyclodedecane as a Model for Carbonic Anhydrase" © 1993 American Chemical Society, Inorganic Chemistry, vol. 32, p. 5749-5755.

International Preliminary Report on Patentability from PCT Application No. PCT/US2011/034620 dated Dec. 6, 2012.

* cited by examiner

SYNTHESIS OF TRIAZOLE-BASED AND IMIDAZOLE-BASED ZINC CATALYSTS

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to triazole-based and imidazole-based Zinc catalysts and precursors, and more particularly, to the synthesis and use of triazole-based and imidazole-based Zinc catalysts useful for the hydration of carbon dioxide, and precursors of such catalysts.

BACKGROUND

The enzyme carbonic anhydrase (CA) (EC 4.2.1.1) is a metalloenzyme (which is an enzyme that includes one or more functional metal atoms) that catalyzes the rapid conversion of carbon dioxide into bicarbonate via a hydration reaction. The catalytic center of the enzyme consists of a Zinc atom coordinated by three histidine residues in the active site in addition to a water molecule that serves as a source of hydroxide ion. Over the years, a number of catalytic systems have been designed in hopes to mimic CA's active site and thus use these synthetic systems to effect the removal of carbon dioxide from the atmosphere and the environment. These efforts have resulted in a number of catalysts possessing the Zinc-bound water molecule and capable of catalyzing the hydration of carbon dioxide with varied efficiency; however, the catalysts still suffer from several drawbacks.

One such drawback lies in the synthetic protocols utilized for the construction of these prior art catalysts, which do not enable a library of Zinc-coordinating scaffolds to be generated for the rapid evaluation and assessment of their catalytic properties. As such, even if a potentially good catalyst candidate may be identified, there are no simple means to chemically modify its structure to further improve its catalytic profile. Furthermore, the catalysts described to date originate from synthetic routes plagued with time consuming purification techniques and the inaccessibility to generate chemical diversity within a designed system since each catalyst is manufactured through the same amount or more steps as the other, with no common intermediate that can be used for scale up production.

Another drawback to these prior art catalysts is the poor to non-existent water-solubility of the catalysts, as reported in literature so far, thus preventing a direct comparison of the catalyst's attributes to those of the active site of CA. Additionally, another drawback is the experimental evidence that the zinc-bound water molecule must possess a $pK_a$ value close to that one exhibited by the CA enzyme ($pK_a$ of about 7.0) to efficiently catalyze the hydration reaction. This key property of a designed catalytic system finds no benefit from the current, restricted synthetic schemes employed for their construction.

Therefore, it would be beneficial to have the ability to prepare a library of diverse scaffolds to construct catalysts, not only to study the catalysts produced, but to directly tune the value of the water's $pK_a$ in the produced catalyst by altering the electronic properties of the triazole rings bound to the Zinc metal via analog synthesis.

SUMMARY

In one embodiment, a complex where R, R', and R" are molecules capable of binding with nitrogen, has the following structure:

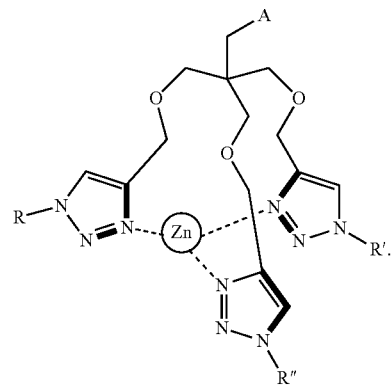

In another embodiment, a complex where R, R', and R" are molecules capable of binding with nitrogen, has the following structure:

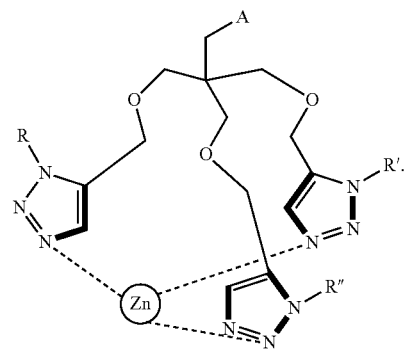

In another embodiment, a complex where R, R', and R" are molecules capable of binding with nitrogen, has the following structure:

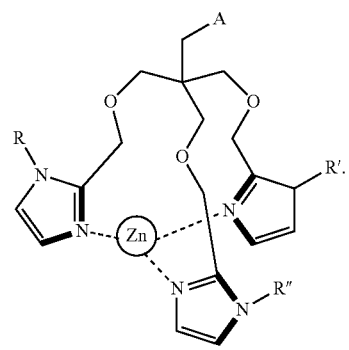

In yet another embodiment, a method for creating a disubstituted triazole molecule includes contacting an alkyne having a R1 group and an azide having a R2 group in the presence of copper(I) to create a 1,4-disubstituted triazole molecule having the R1 group and the R2 group according to the following reaction:

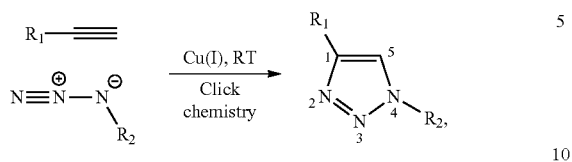

wherein the R1 group is a molecule capable of binding with carbon and the R2 group is a molecule capable of binding with nitrogen.

According to another embodiment, a method for creating a tris(imidazolyl)pentaerythritol molecule includes alkylating an imidazole 2-carbaldehyde molecule (1) to create a monoalkylated aldehyde molecule (2), reducing the monoalkylated aldehyde molecule (2) to create an alcohol intermediate molecule (3), converting the alcohol intermediate molecule (3) to create an alkyl halide molecule (4) using a thionyl halide, and reacting the alkyl halide molecule (4) with a pentaerythritol molecule to create a tris(imidazolyl)pentaerythritol molecule. Creating the tris(imidazolyl)pentaerythritol molecule is carried out according to the following equation:

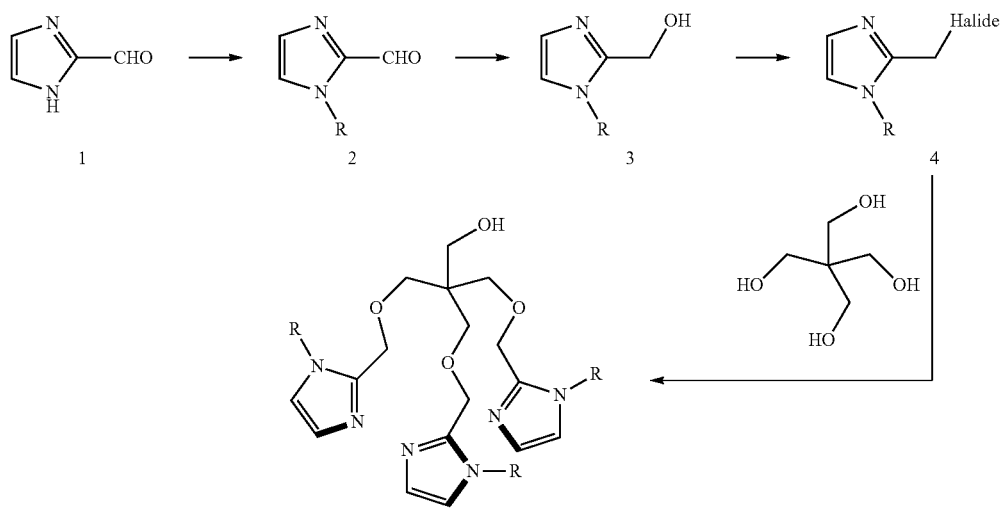

In another embodiment, a method for creating a tris(triazolyl)pentaerythritol molecule includes contacting a pentaerythritol molecule with a propargyl halide molecule to create a trialkyne intermediate molecule, and contacting the trialkyne intermediate molecule with an azide molecule having a R group to create a tris(triazolyl)pentaerythritol molecule. Each R group is a molecule capable of binding with nitrogen, and producing the tris(triazolyl)pentaerythritol molecule is carried out according to the following reaction:

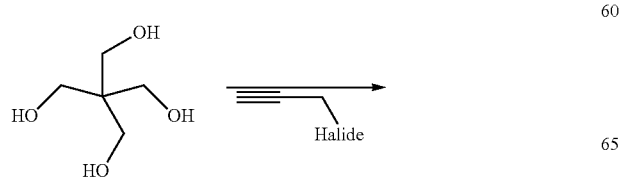

-continued

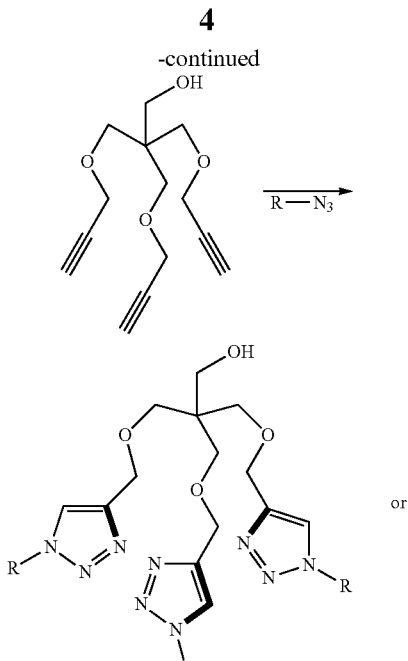

or

-continued

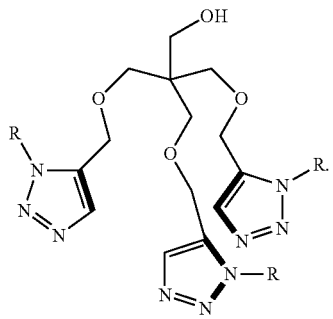

According to yet another embodiment, a method for creating a tris(triazolyl)pentaerythritol molecule, where each R group is a molecule capable of binding with carbon, includes contacting a tris(azido)pentaerythritol molecule (8) with an alkyne molecule having a R group to create a tris(triazolyl) pentaerythritol molecule (9) according to the following reaction:

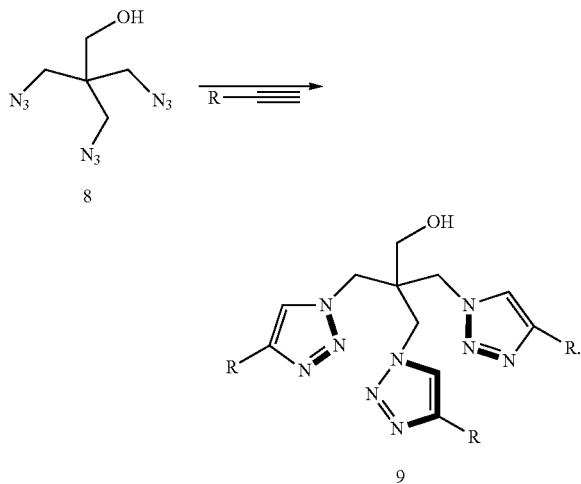

Other aspects and embodiments of the present invention will become apparent from the following detailed description, which, when taken in conjunction with the drawings, illustrate by way of example the principles of the invention.

DETAILED DESCRIPTION

Figure 1:
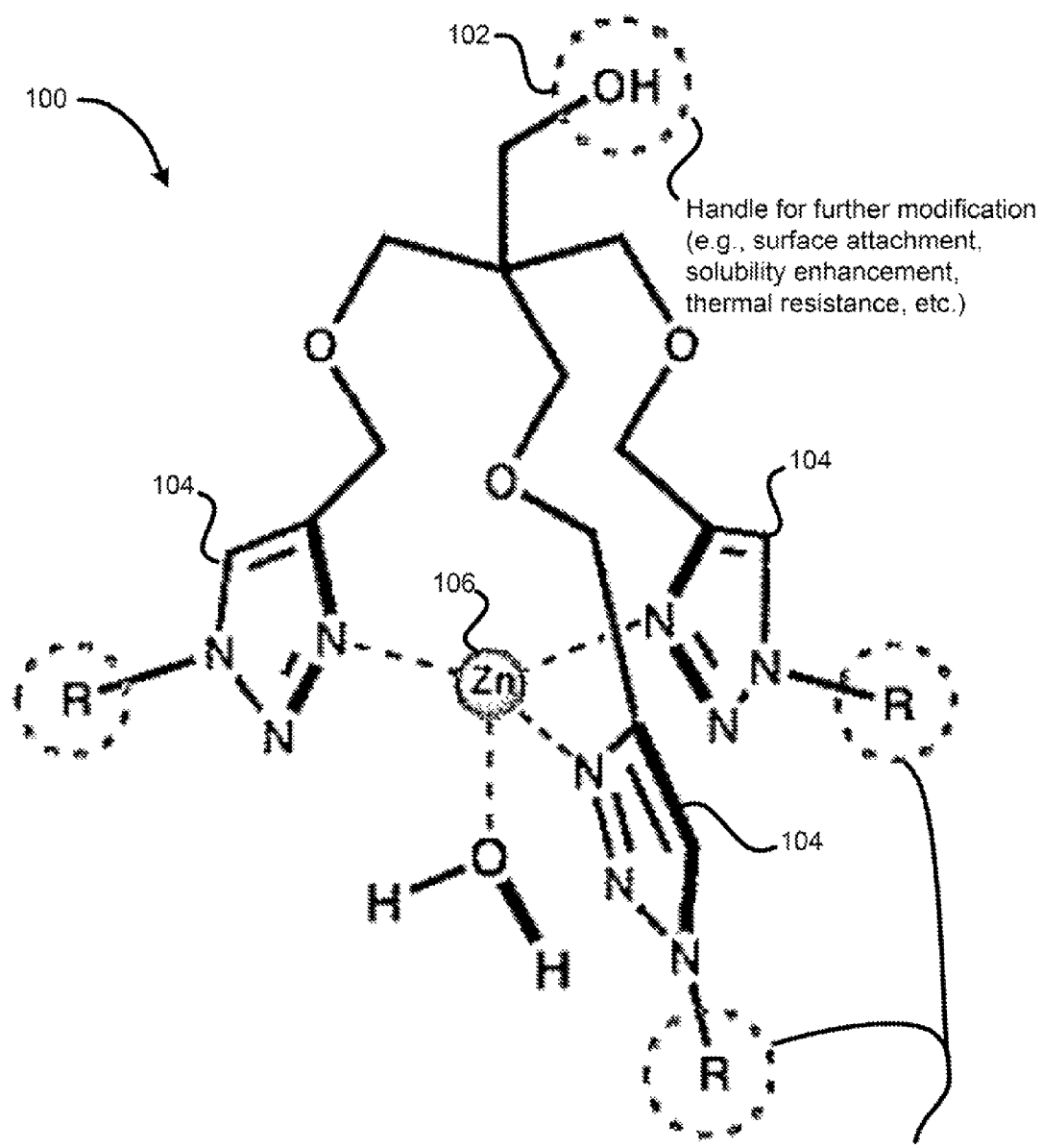
FIG. 1 shows a general structure of a tris(triazolyl)pentaerythritol catalyst system, in accordance with one embodiment.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

In one general embodiment, a complex where R, R', and R" are molecules capable of binding with nitrogen, has the following structure:

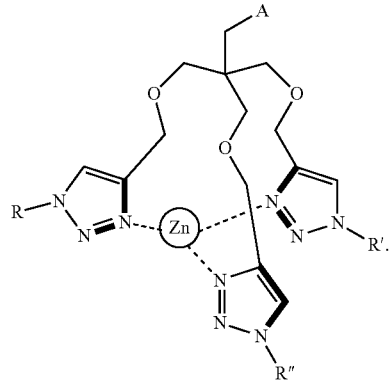

In another general embodiment, a complex where R, R', and R" are molecules capable of binding with nitrogen, has the following structure:

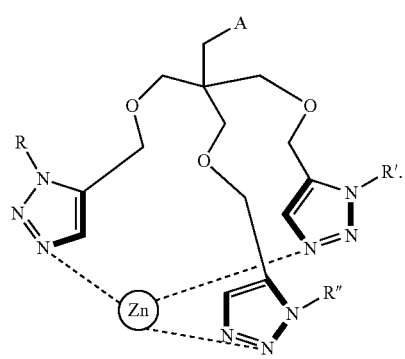

In another general embodiment, a complex where R, R', and R" are molecules capable of binding with nitrogen, has the following structure:

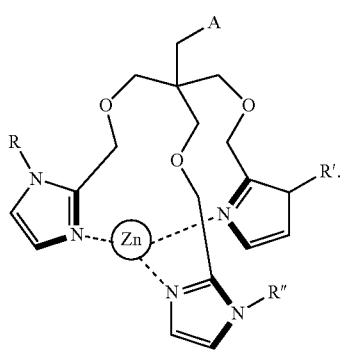

In yet another general embodiment, a method for creating a disubstituted triazole molecule includes contacting an alkyne having a R1 group and an azide having a R2 group in the presence of copper(I) to create a 1,4-disubstituted triazole molecule having the R1 group and the R2 group according to the following reaction:

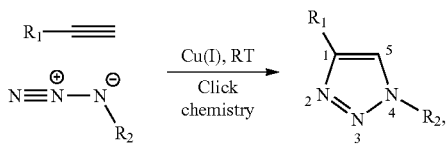

wherein the R1 group is a molecule capable of binding with carbon and the R2 group is a molecule capable of binding with nitrogen.

According to another general embodiment, a method for creating a tris(imidazolyl)pentaerythritol molecule includes alkylating an imidazole 2-carbaldehyde molecule (1) to create a monoalkylated aldehyde molecule (2), reducing the monoalkylated aldehyde molecule (2) to create an alcohol intermediate molecule (3), converting the alcohol intermediate molecule (3) to create an alkyl halide molecule (4) using a thionyl halide, and reacting the alkyl halide molecule (4) with a pentaerythritol molecule to create a tris(imidazolyl)pentaerythritol molecule. Creating the tris(imidazolyl)pentaerythritol molecule is carried out according to the following equation:

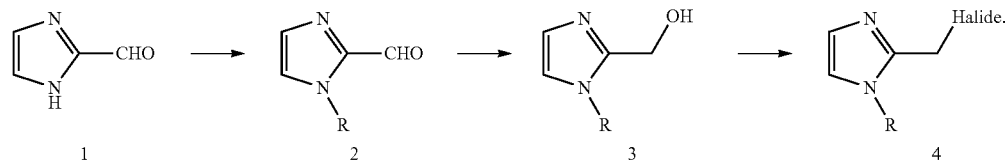

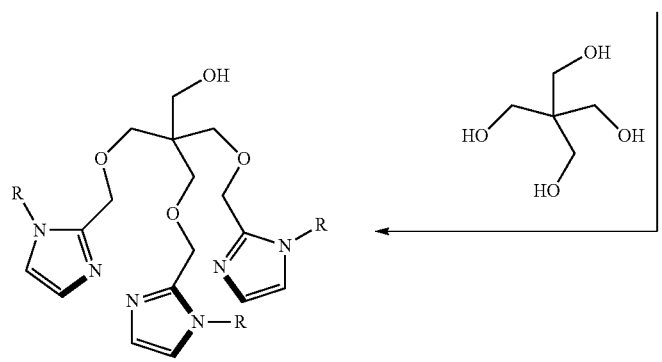

In another general embodiment, a method for creating a tris(triazolyl)pentaerythritol molecule includes contacting a pentaerythritol molecule with a propargyl halide molecule to create a trialkyne intermediate molecule, and contacting the trialkyne intermediate molecule with an azide molecule having a R group to create a tris(triazolyl)pentaerythritol molecule. Each R group is a molecule capable of binding with nitrogen, and producing the tris(triazolyl)pentaerythritol molecule is carried out according to the following reaction:

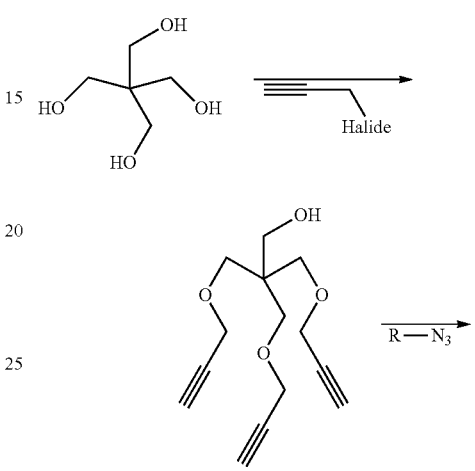

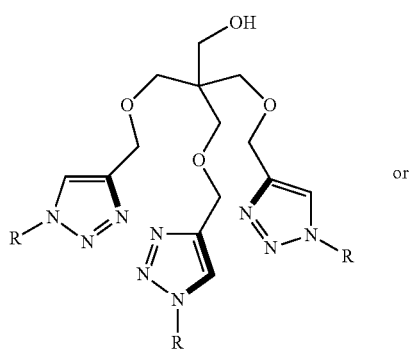

or

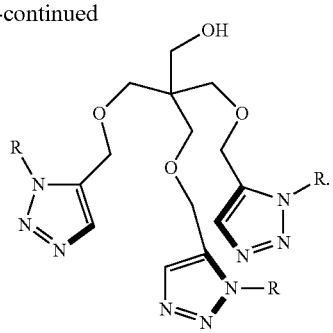

According to yet another general embodiment, a method for creating a tris(triazolyl)pentaerythritol molecule, where each R group is a molecule capable of binding with carbon, includes contacting a tris(azido)pentaerythritol molecule (8) with an alkyne molecule having a R group to create a tris (triazolyl)pentaerythritol molecule (9) according to the following reaction:

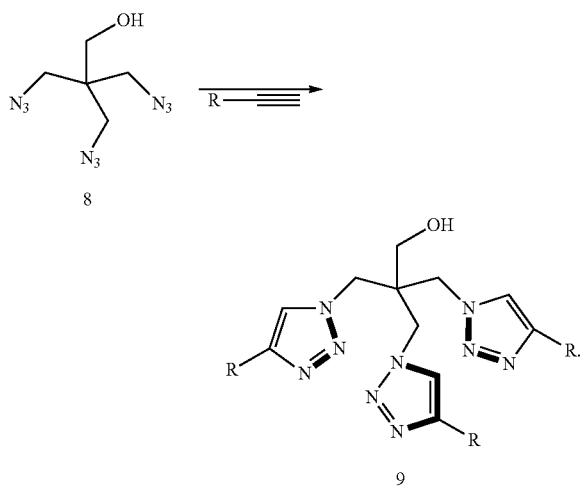

Disclosed herein are systems and methods for the efficient synthesis, using Click chemistry (e.g., the Cu(I)-catalyzed Huisgen cycloaddition reaction between azides and terminal alkynes to yield triazoles), of tris-triazolyl Zinc scaffolds capable of catalyzing the hydration of carbon dioxide to yield a bicarbonate, according to various embodiments. Click chemistry is a general term that refers to a chemical philosophy or technique which relies on generating large compounds reliably and quickly from smaller, more easily manipulated units making use of high-yielding and highly predictable chemical transformations. The scaffolds described herein possess three triazole rings whose nitrogen atoms serve as coordination points to the Zinc metal center and use it as a platform to perform the hydration of carbon dioxide, according to some approaches. The triazole cores have been chosen for several reasons, including: 1) their excellent coordinating properties to Zinc, 2) their Zinc-adducts have not previously been evaluated as catalysts for carbon dioxide hydration, and 3) the synthesis of the proposed scaffolds can be accomplished using the Cu(I)-catalyzed dipolar cycloaddition reaction (using Click chemistry), a method that brings not only speed and library access to the approach, but also efficiency, as purification steps are minimized throughout the synthetic process, according to preferred embodiments. The synthesis of a large library of these triazole-bearing scaffolds enables the study of the triazole ring as a candidate in the design of Zinc-centered catalysts for the hydration of carbon dioxide as a large number of analogs can be prepared and screened. In addition to the reasons cited above, the scaffolds described herein possess an additional chemical functionality in their make-up that can be used for tuning the catalyst's properties, such as increasing their water-solubility, enabling their attachment to a variety of surfaces, etc.

According to one embodiment, the use of 1,2,3-triazoles, constructed in a concise and expedient manner using Click chemistry, may be used as scaffolds for the formation of Zinc-centered complexes capable of catalyzing the hydration of carbon dioxide. The general structure of the catalyst 100 is shown in FIG. 1, according to one embodiment.

There are three features of particular interest in the catalyst's framework. The first one is the available hydroxymethyl moiety 102 which may serve as a chemical handle for further elaboration of the catalyst 100, such as the addition of particularly useful functional groups to alter a characteristic of the catalyst 100, such as thermal stability, solubility, electrical properties, etc. One of these modifications of the hydroxymethyl group 102 is its elongation with a functional group or functionality that can be used later as a surface attachment tethering group.

The catalyst 100, as shown in FIG. 1, includes three R groups bound to one nitrogen from each triazole ring, in one embodiment. In this embodiment and any other presented herein, including those shown in FIGS. 4A-4C, even though each R group is indicated by the same symbol (R), each may be a different group capable of binding to a nitrogen. In this way, there may be a R group, a R' group, and a R" group, and each may be a different nitrogen bound group, such as a —$C_2O(OR)$ group, —$C_2NR_2$ group, —$C_2OH$ group, a —$SO_3^{-2}$ group, etc., where the R here can be any atom or molecule, as would be known to one of skill in the art. For example, in one approach, R may be a molecule capable of binding with nitrogen, R' may be the same or a different molecule capable of binding with nitrogen, and R" may be the same molecule (either R or R') or a different molecule capable of binding with nitrogen.

Figure 2A:
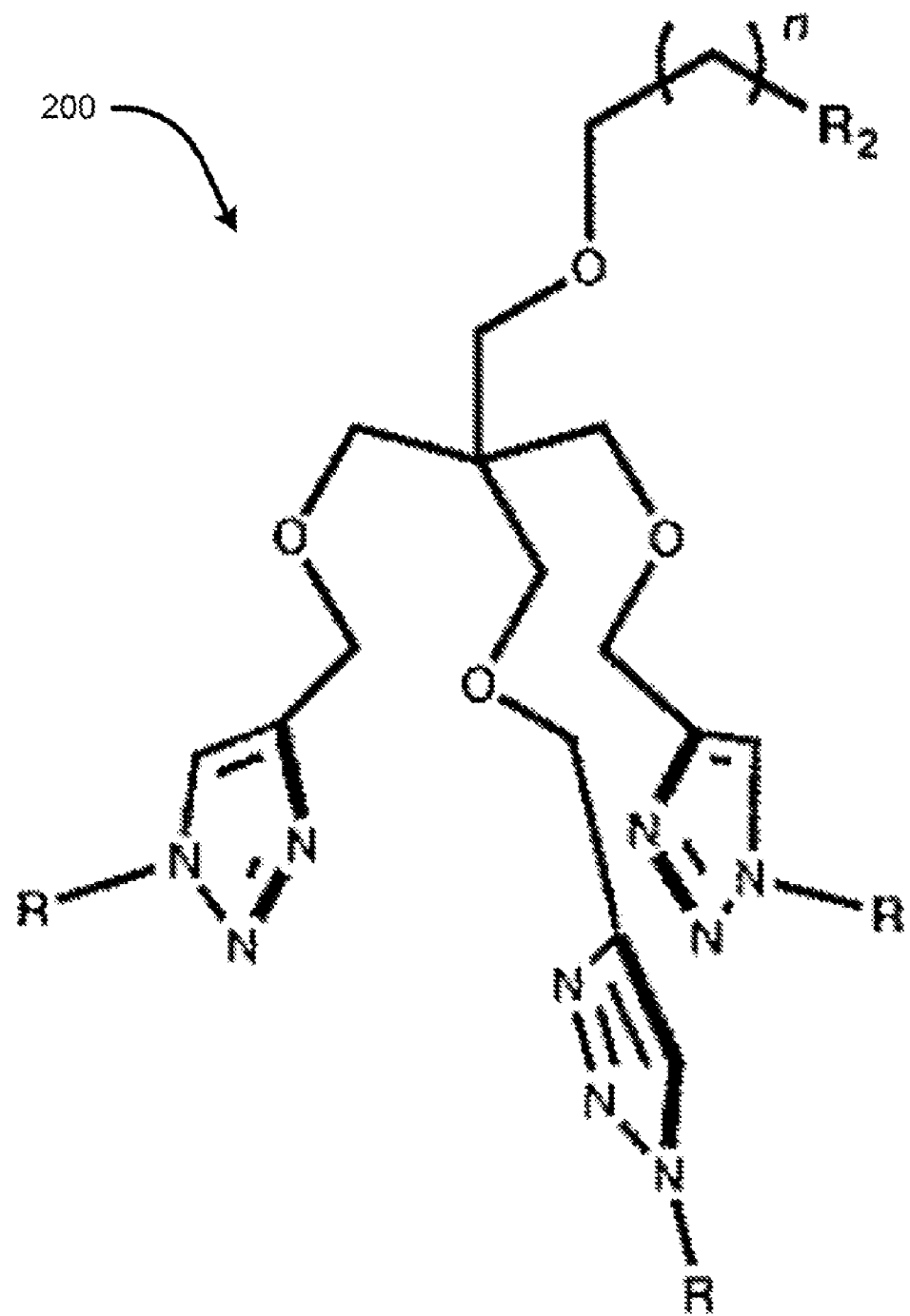
FIG. 2A shows a tris(triazolyl)pentaerythritol molecule that has a chemically modified hydroxymethyl group, according to one embodiment.

FIG. 2A shows a molecule 200, similar to the catalyst 100 from FIG. 1, but without the complexed Zinc and water molecule and modified at the hydroxymethyl group, which can produce many desired effects and characteristics, depending on the modifying group that is added and length of the monomeric or polymeric tether (if present) of n atoms long, according to various embodiments. The R2 group may be any functional group which achieves a desired characteristic for the molecule 200, such as a —SH group, —$Si(OR)_3$ group, —$N_3$ group, —$NH_2$ group, —S—SR group, etc. For example, one can anticipate that the presence of a thiol group (—SH) may be used for attachment of the molecule 200 to surfaces, nanoparticles, microparticles, or some other structure comprised of gold. Of course, other functional groups may provide the ability for attachment to other materials, such as silver, platinum, tungsten, etc., and combinations thereof. In another example, the presence of a triethoxysilyl ether moiety (—Si $(OR)_3$) may be used for the attachment of the molecule 200 to a glass coating, glass surface, glass particles, etc.

Figure 2B:
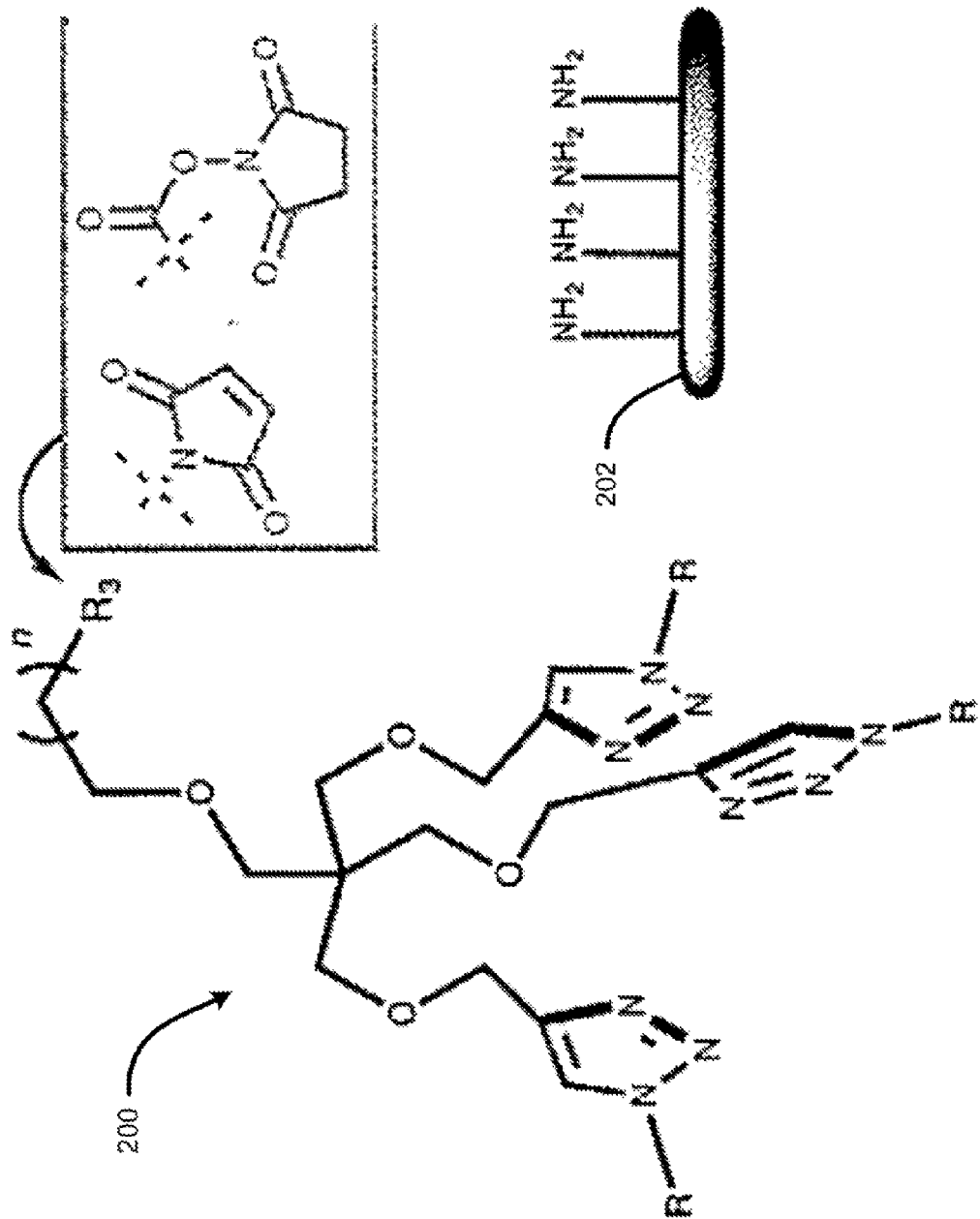
FIG. 2B shows a possible hydroxymethyl group modification resulting in conjugation to a surface for the tris(triazolyl) pentaerythritol molecule, according to one embodiment.
Figure 2C:
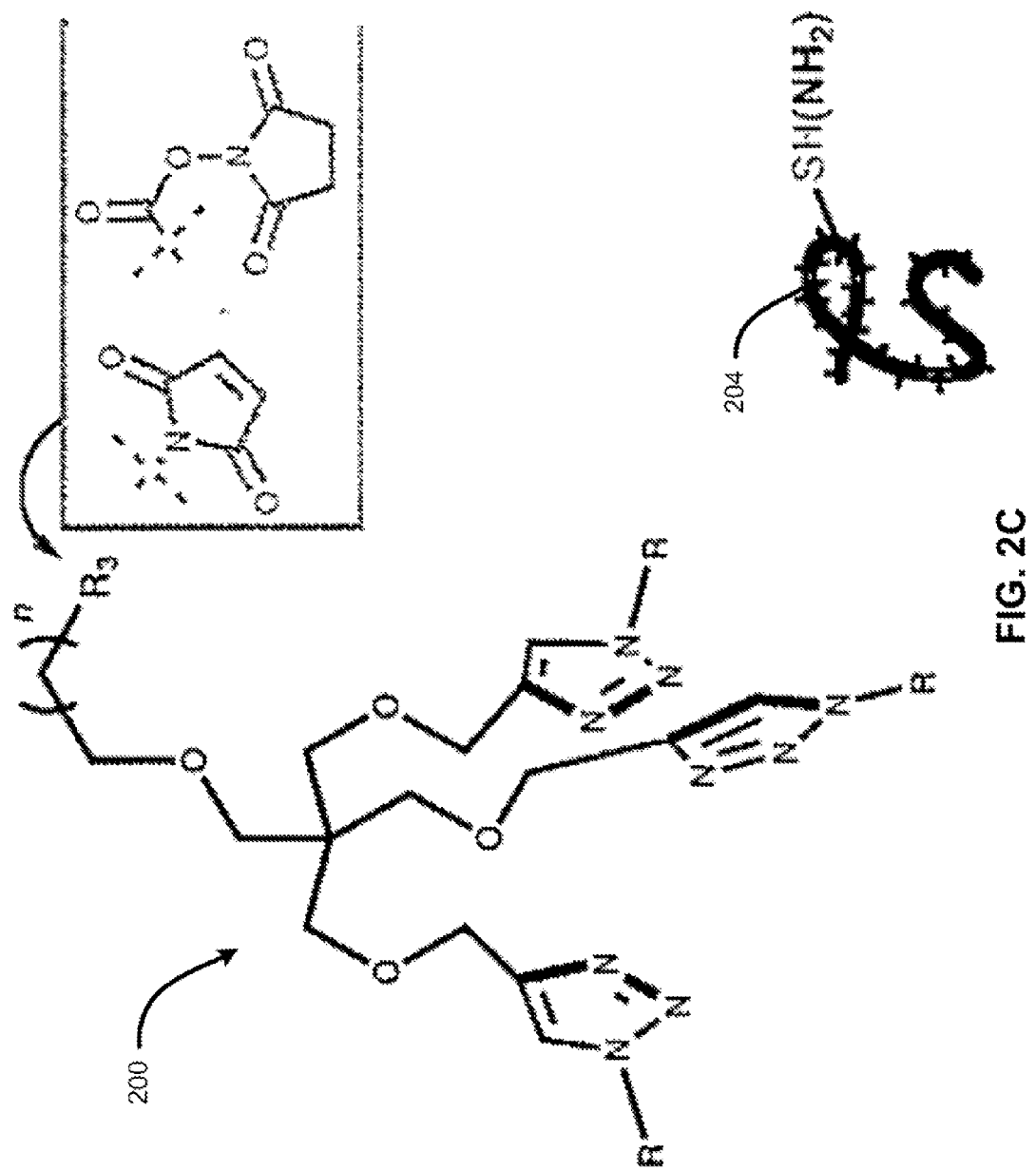
FIG. 2C shows a possible hydroxymethyl group modification for the tris(triazolyl)pentaerythritol molecule resulting in conjugation to a target of interest, according to one embodiment.

Naturally, more elaborate modifications of the hydroxymethyl group (102, FIG. 1) into functionalities that are reactive against other functionalized surfaces may be achieved, as shown in FIG. 2B, such as a surface 202 treated to have a plurality of alkyne groups present. In FIG. 2C, biological targets 204 may be attracted/attached to the molecule 200, such as cysteines or lysines in proteins by activation via the N-hydroxysuccinimidyl and maleimide groups, respectively, in some approaches.

Referring again to FIG. 1, for example, assuming that a protein is chosen for its availability and low cost, such as Bovine Serum Albumin (BSA), the glutamic/aspartic residue acids that are present on the BSA can be modified such that the catalyst 100 can be bound to the BSA molecule via its hydroxymethyl group 102. In another example, the carboxylic acid sidechains (from glutamate or aspartate amino acid residues) on the BSA may be used to label the protein with catalyst 100, and this may be performed by activating the sidechain's carboxylates for conjugation to the catalyst 100 off of that hydroxymethyl group 102, such that the BSA is covalently tagged with the catalyst 100. Conversely, the protein can attack the catalyst and modify itself with the catalyst by activating catalyst 100 for a nucleophilic attack by BSA's lysine residues. Thus, chemically speaking, the protein can be used as a nucleophile to attack an electrophile on the catalyst, or the catalyst can be used as a nucleophile to attack the protein's carboxylate or active carboxylic acid residues that would result in its modification as well.

Figure 3:
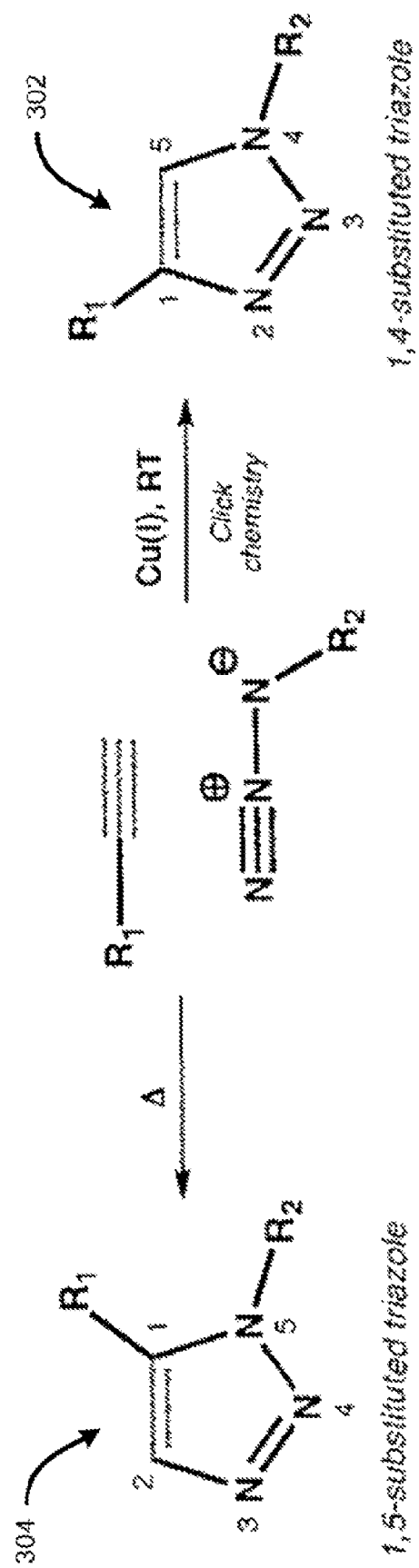
FIG. 3 shows formation of 1,5- and 1,4-disubstituted triazoles via a thermal and a Cu(I)-catalyzed 1,3 dipolar (Click chemistry) cycloaddition route, according to several embodiments.

With continued reference to FIG. 1, a second feature of the catalyst 100, according to some approaches, are the triazole rings 104 which serve as the coordinating elements to the Zinc metal 106. The use of Click chemistry to assemble the catalyst 100, according to one embodiment, generates the 1,2,3-triazole rings 104 exhibiting a 1,4-substitution pattern 302, as shown in FIG. 3 on the right side, according to one embodiment. Once the preliminary screening of these 1,4-substituted catalysts 302 have yielded the most promising hits, the synthesis of their corresponding 1,5-regioisomers 304 may be undertaken and points of comparison drawn between them based on their catalytic properties and stability profiles. The synthesis of the 1,5-regioisomers 304 is straightforward as it involves the heating of the alkyne and the azide components to give a 1:1 mixture of the 1,4- and 1,5-substituted products, easily separable by chromatographic methods, as it would be known to one of skill in the art, according to one embodiment. Naturally, other ratios are possible also, such as a range from about 2:1 1,4- to 1,5-substituted products to about 1:2 1,4- to 1,5-substituted products.

As shown in FIG. 3, the 1,4- and 1,5-substituted triazole products each have an R1 group previously part of the alkyne and a R2 group previously part of the azide. These R groups may be the same or different, and may be any molecule, as would be known to one of skill in the art, which may bind to the 1,4- and 1,5-substituted triazole products as shown in FIG. 3, including those R groups disclosed herein and any other. For example, the R1 group may be a molecule capable of binding with carbon and the R2 group may be a molecule capable of binding with nitrogen.

Figure 4A:
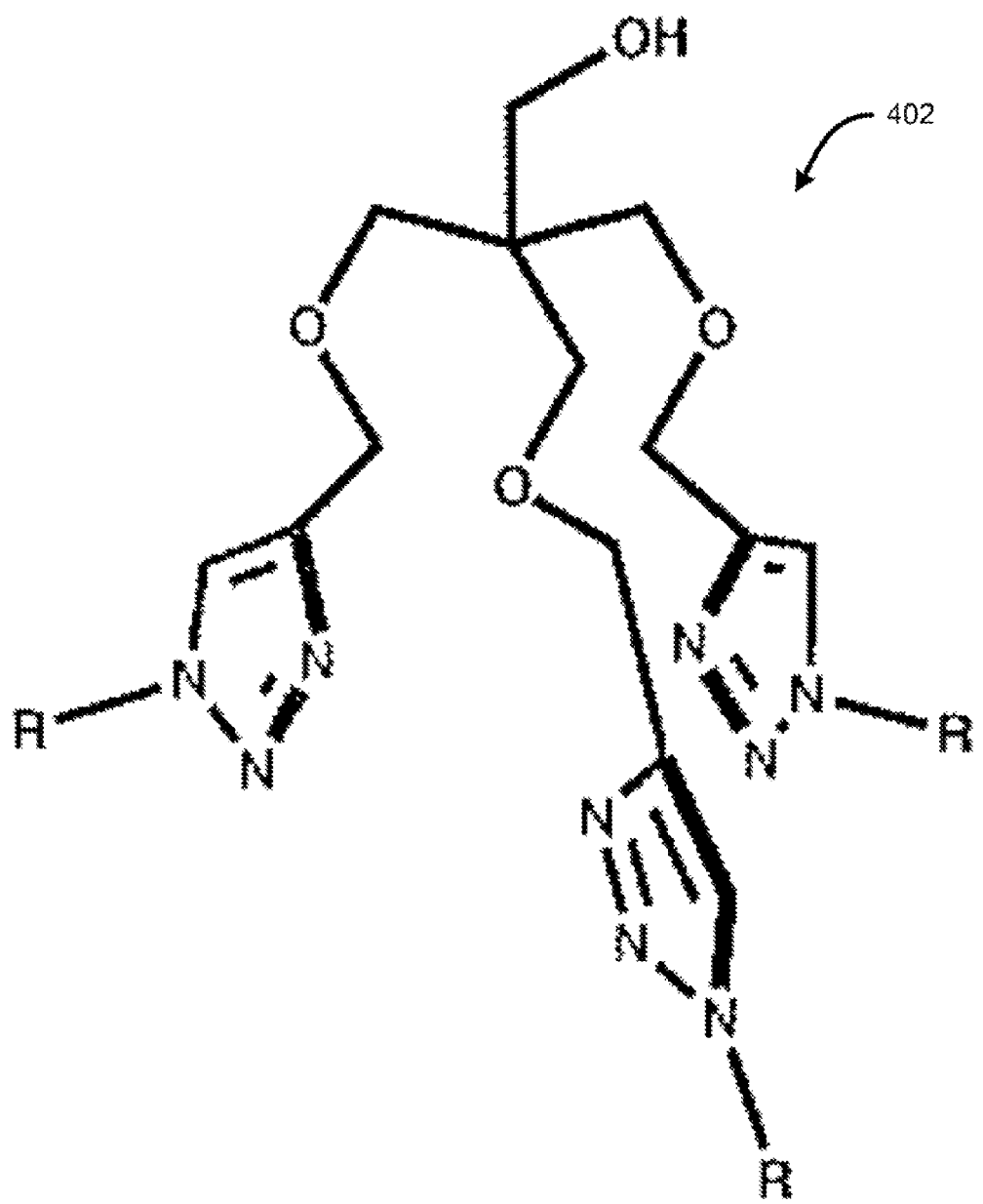
FIG. 4A shows a tris(1,4-triazolyl)pentaerythritol molecule, according to one embodiment.
Figure 4B:
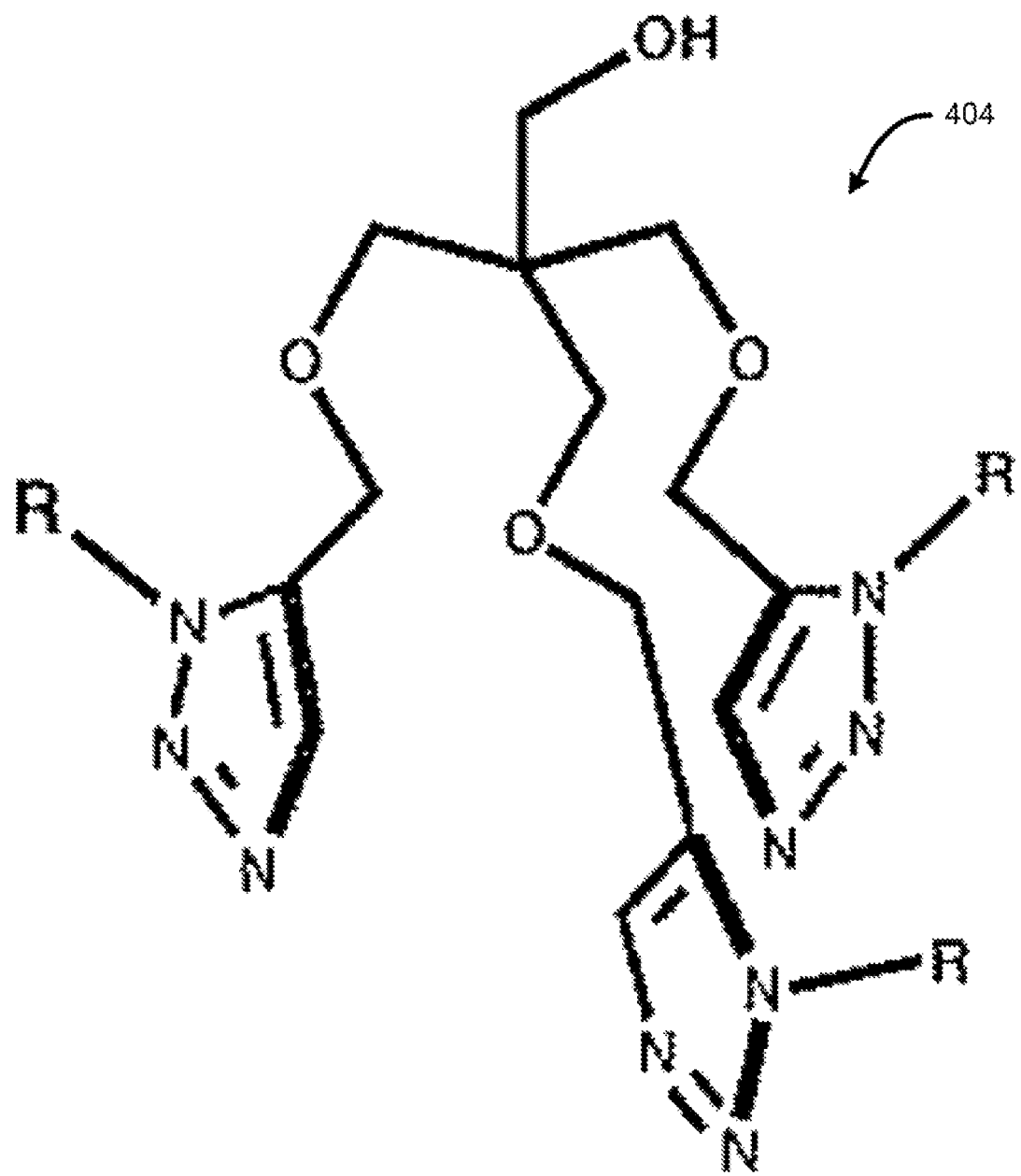
FIG. 4B shows a tris(1,5-triazolyl)pentaerythritol molecule, according to one embodiment.
Figure 4C:
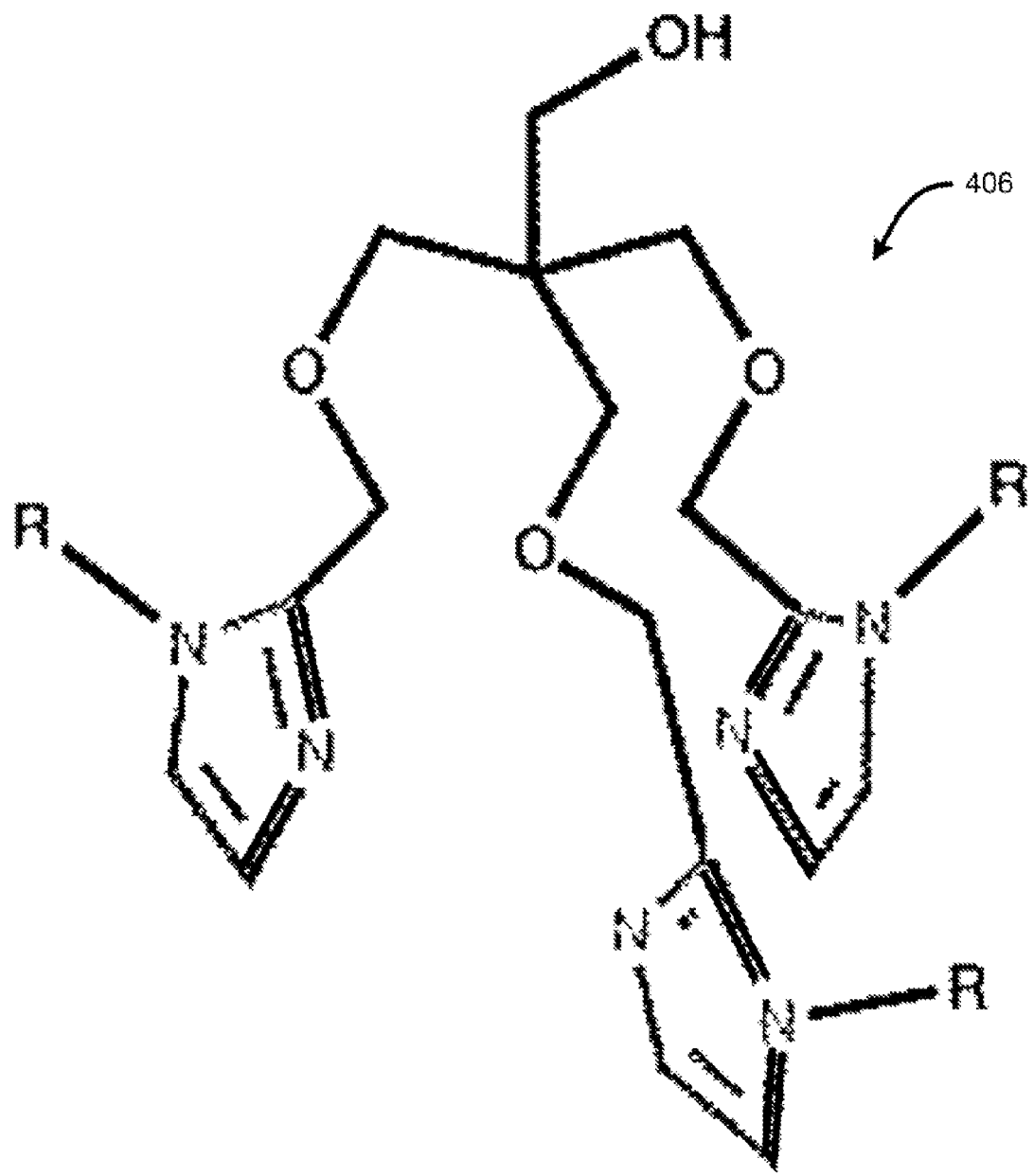
FIG. 4C shows a Iris(C2-imidazolyl)pentaerythritol molecule, according to one embodiment.

The 1,4- and 1,5-substituted triazole products 302, 304 may possess unique properties once they have formed their Zinc complexes. Such difference is believed to arise not only from their differences in electronic properties and dipole moments of the triazole rings but also from the significantly different orientation of the R groups in both cases, as shown in FIGS. 4A and 4B, according to one embodiment. FIG. 4C shows another variation suitable for use, with C2-imidazoles present in place of the triazoles, according to another embodiment. Another interesting feature of the triazole rings is their degree of mimicking potential of the imidazole rings found in the histidine residues residing in the catalytic site of CA.

In FIG. 4A, the molecule 402 includes triazoles that are 1,4-substituted, like the 1,4-substituted products 302 in FIG. 3. Referring again to FIG. 4A, looking at the nitrogen molecules in the triazoles, the nitrogen which has an attached R group is pointing toward the exterior of the molecule 402. This means that the nitrogen which is double-bonded to the middle nitrogen and single-bonded to the carbon atom (the actual Zinc-coordinating nitrogen) is positioned toward the interior of the molecule 402. This provides for space in the middle of the molecule 402 for a Zinc atom to bind to the interior facing nitrogen atoms. In this molecule 402, if the Zinc atom is bound to the interior three nitrogen atoms of the three triazoles, most likely, the Zinc atom is going to be protected deep in that "pocket", according to one embodiment.

The only difference between the molecule 402 shown in FIG. 4A and the molecule 404 shown in FIG. 4B is that there are three 1,5-substituted triazoles, similar to the 1,5-substituted triazole products 304 in FIG. 3. Referring again to FIG. 4B, the nitrogen which is double-bonded to the middle nitrogen and single-bonded to the carbon atom is positioned toward the lower portion of the molecule 404, and not oriented inward. In some embodiments, if a Zinc atom is bound to these nitrogen atoms, the Zinc atom will most likely coordinate and sit towards the exterior of the molecule 404, thereby resulting in a different complex than that produced with a 1,4-triazole, which might result in a completely different binding mode altogether, in some approaches.

Now referring to FIG. 4C, this molecule 406 includes imidazole rings instead of triazole rings. A Zinc atom may be bound to this molecule 406 at the nitrogen of each imidazole ring which is double-bonded to carbon on one side and single-bonded to carbon on the other side. In addition, these nitrogen binding sites are facing inward, thereby providing similar beneficial effects as that of molecule 402 in FIG. 4A. In some embodiment, the enzyme in the natural reaction (not including copper as a catalyst) uses histidine residues in the catalytic site of CA, and as imidazoles are part of histidines, these represent a class of catalysts with a close structural similarity to the enzyme's catalytic machinery. Therefore, molecule 406 in FIG. 4C provides for good comparison to see how well the other molecules (402, 404, FIGS. 4A, 4B, respectively) do against molecule 406 in FIG. 4C, along with an alternate embodiment that can be used in practice.

Scheme 1

Figure 5:
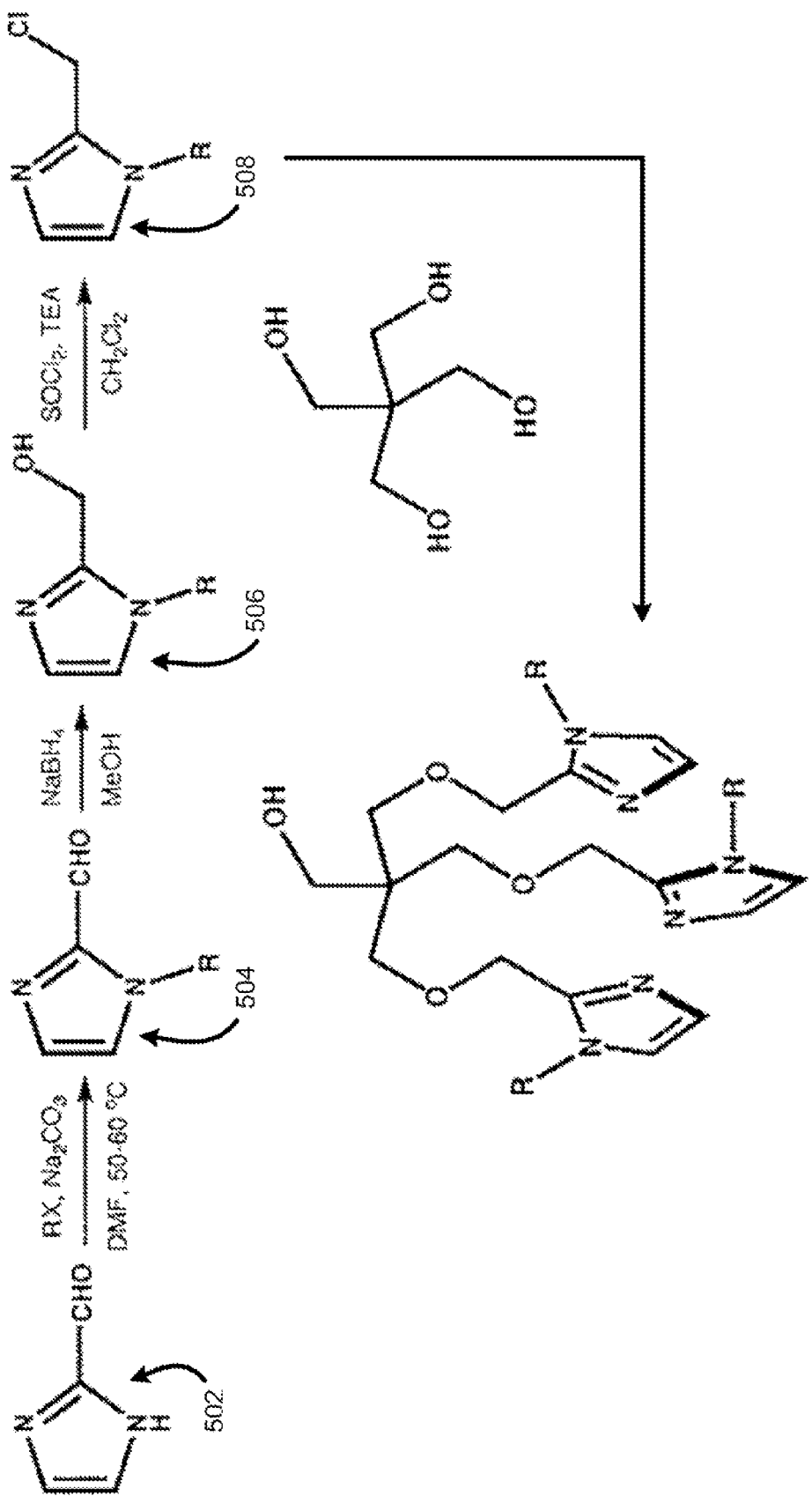
FIG. 5 shows the synthesis of 2-chloromethylimidazolide and its use in the alkylation of pentaerythritol to yield a tris(imidazole)-based system, according to one embodiment.

According to one embodiment, synthesis of 2-chloromethylimidazolide and its use in the alkylation of pentaerythritol to yield the tris(imidazole)-based system is discussed (Scheme 1, as shown in FIG. 5). The synthesis of a tris (imidazolyl) pentaerythritol system has not been described in the prior art, and a synthetic route is described in FIG. 5, according to one embodiment.

The synthesis, in one approach, may start with the alkylation of one of the nitrogen groups in an imidazole 2-carbaldehyde 502 (which may be obtained from a commercial vendor) to give a monoalkylated aldehyde product 504. It is noted that if the tris(imidazolyl) pentaerythritol compounds provide good catalytic activity, then diversity may be introduced at this initial alkylation step using various alkyl halides and aryl halides, in one approach. Reduction of the C2-aldehyde 504 and conversion of the generated C2-alcohol intermediate 506 to the C2-alkyl chloride 508 using thionyl chloride is well known in the art and will produce the alkylating agent, in one approach. Thus, reaction between C2-alkyl chloride 508 with pentaerythritol may yield the tris(imidazolyl) pentaerythritol target system, in some approaches. As in the previous alkylation of pentaerythritol with propargyl bromide, the same procedure may be followed for the installation of the three imidazole units or different procedures may be employed, according to several approaches. Naturally, this protocol to furnish the imidazole counterparts does not enjoy the benefit of easier production and purification, as does its triazolyl counterparts produced via Click chemistry (as described later). However, their synthesis is possible using this method, and is valuable as these systems can serve as catalytic activity reference points to their regioisomeric triazolyl counterparts.

Figure 6:
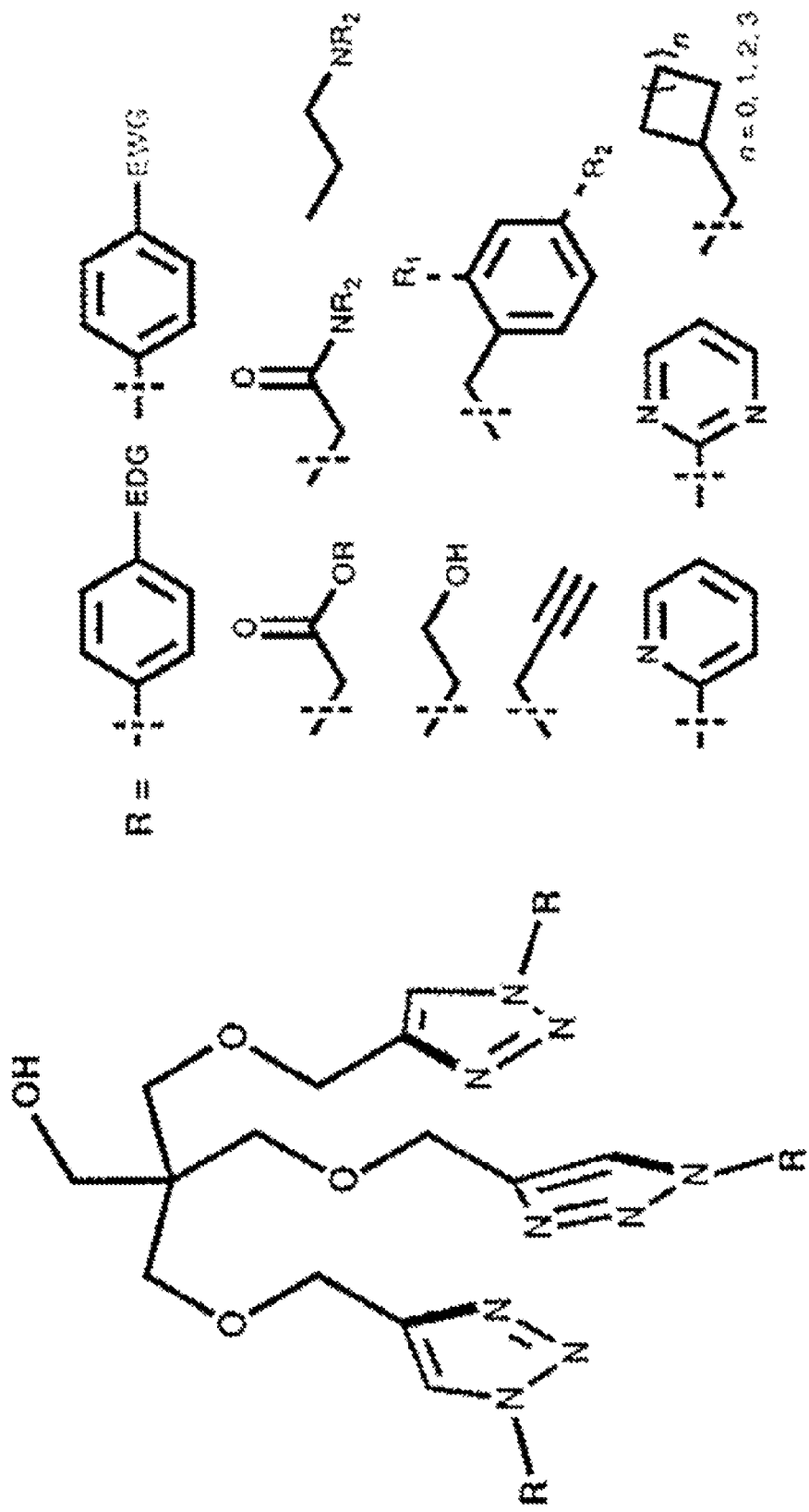
FIG. 6 shows several R group modifications to the triazole-bearing molecule, according to several embodiments.

Another feature of the catalyst is the nature of the R groups. The R group can be used to modulate the electronic properties of the triazole rings or imidazole rings by choosing electron-withdrawing groups (EWG) and/or electron-donating groups (EDG), as shown in FIG. 6 according to one embodiment. Note that EDG represents any Electron-Donating functional Group while EWG represents any Electron-Withdrawing functional Group, of which there are a considerable number of each. In FIG. 6, the structure having the imidazole rings is not shown, but the approaches described hereafter are possible with the structure having the imidazole rings, as shown in FIG. 4C. Not only is the binding ability of the triazole rings or imidazole rings to Zinc affected by these changes, but also their catalytic properties as the R group directly exerts electronic effects on the triazole ring or imidazole ring as a result of its close proximity and direct conjugation in the case of the aryl azides, as shown in FIG. 6, in one approach. For the sake of clarity, the rest of the discussion regarding the R groups will refer to the triazole rings alone, but apply equally to the imidazole rings as well.

For the R groups, almost any group may be used that has an azide on it or that may have an azide attached to it, because the reaction utilizes the azide to form the triazole ring. Now, with regard to the nature of the R group, its identity will have a profound effect on the physical properties of the catalyst, because when the Zinc is triazole-bound, the strength of such binding will be highly dependent on the electron density of the triazole heterocycle. In one example, if an R group is placed, such as a phenyl ring bearing an EWG, the catalytic power of the molecule may be decreased as the Zinc-nitrogen bond may be weakened by the action of the EWG. Conversely, the use of a phenyl ring bearing an EDG may result in the opposite effect, thereby increasing the catalytic power of the molecule. So, the speed of the reaction may be modulated by carefully selecting the chosen functional group.

In another example, a catalyst may be produced that possesses marginal solubility in water. In this example, the R group added may be a sulfate functionality, such that it improves the catalyst's water solubility. In another example, for the synthesis of more heat resistant catalysts, the R group added may be more bulky, such as an alkyl group, or a very extended chain of carbons, so the activity and the stability of the catalyst may be tuned based on the R groups that are used.

Furthermore, the R group may be modulated in a manner that addresses potentially negative attributes of a good catalyst candidate, such as water solubility (R group may become a $—SO_3^{-2}$ group, a PEG-like moiety, etc.), or some other property of the catalyst.

Another feature of the catalyst is the remaining hydroxyl group positioned at the head of the catalyst, and this hydroxyl group can be used to address solubility issues or whenever surface binding is desired.

Scheme 2

Figure 7:
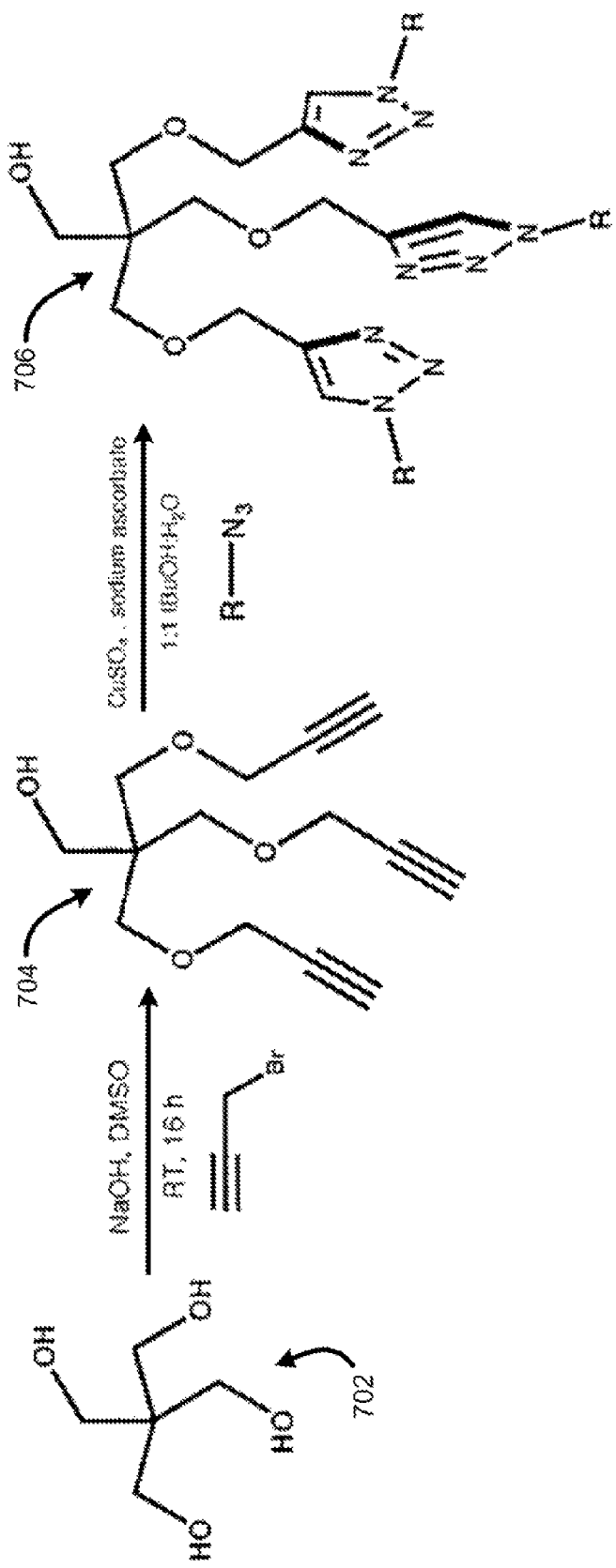
FIG. 7 shows the synthesis of an intermediate trialkynyl-pentaerythritol and its derivatization via Click chemistry to produce a library of tris(triazolyl)pentaerythritol scaffolds, according to one embodiment.

According to one embodiment, the synthesis of the proposed scaffolds is shown in FIG. 7 and it is noted that the use of Click chemistry enables the production of a library of catalysts of which the better ones can undergo further study and improvement, over time and as needs of the catalysts change. In FIG. 7, the synthesis of intermediate trialkynyl-pentaerythritol 704 and its derivatization via Click chemistry to produce a library of tris(triazolyl)pentaerythritol scaffolds with the general structure of 706 is shown according to one embodiment.

Regarding the synthetic aspects of the production process, it is also noted that the materials chosen for the construction of the catalysts are inexpensive (when compared to materials used in other production processes) and readily available. Additionally, the steps used for their construction, most specifically the one(s) involving Click chemistry, are not only high-yielding (which enables the gram-scale preparation of key intermediates), but substantially aided by simple purification techniques such as filtration. Their purification via filtration is helpful as it eliminates the use of time-consuming column chromatographic methods for their isolation. Thus, the synthesis of the catalyst begins with inexpensive, readily available (in bulk quantities) materials, such as pentaerythritol, which is available for as little as $20 per kilogram. Referring again to FIG. 7, pentaerythritol 702 is subjected to a trialkylation with propargyl bromide to give the trialkyne-bearing intermediate 704 (up to about 78%). Intermediate 704 may be prepared in multigram quantities and then reacted with a library of azide-bearing compounds to give the final tris(triazolyl) scaffold 706 using the Cu(I)-catalyzed Huisgen cycloaddition commonly known as Click chemistry.

The azides in the synthesis can be obtained from commercial sources or can be prepared in one or two steps from their commercially available, precursor alkyl/aryl halides. Moreover, the synthesis can be simplified even further, in the case of the alkyl azides, as once the tris(alkynyl)pentaerythritol compound 704 is made, it can be converted directly to the final tris(triazolyl) scaffold 706 by combining it with the alkyl halide and sodium azide, according to one embodiment. In this embodiment, the sodium azide reacts with the alkyl halide and generates the alkyl azide in situ which then, under the Cu(I)-catalyzed conditions, forms the triazole product immediately. Virtually any alkyl or aryl halide may be converted into the azide counterpart via direct nucleophilic displacement (alkyl halides) or $S_NAr$ type reactions on the aryl halides or aryl diazonium salts (obtained from the aryl amines via diazotization with sodium nitrite or isobutyl nitrite) to produce the aryl azides, in some approaches. Once again, full purification of the azides is not necessary as the triazole formation step results in the triazole product that is expected to precipitate from the reaction solution. One feature of the synthesis of the catalysts is that the triazole-bearing products precipitate out of the reaction mixture, thus making their isolation via filtration a simple task to perform.

Scheme 3

Figure 8:
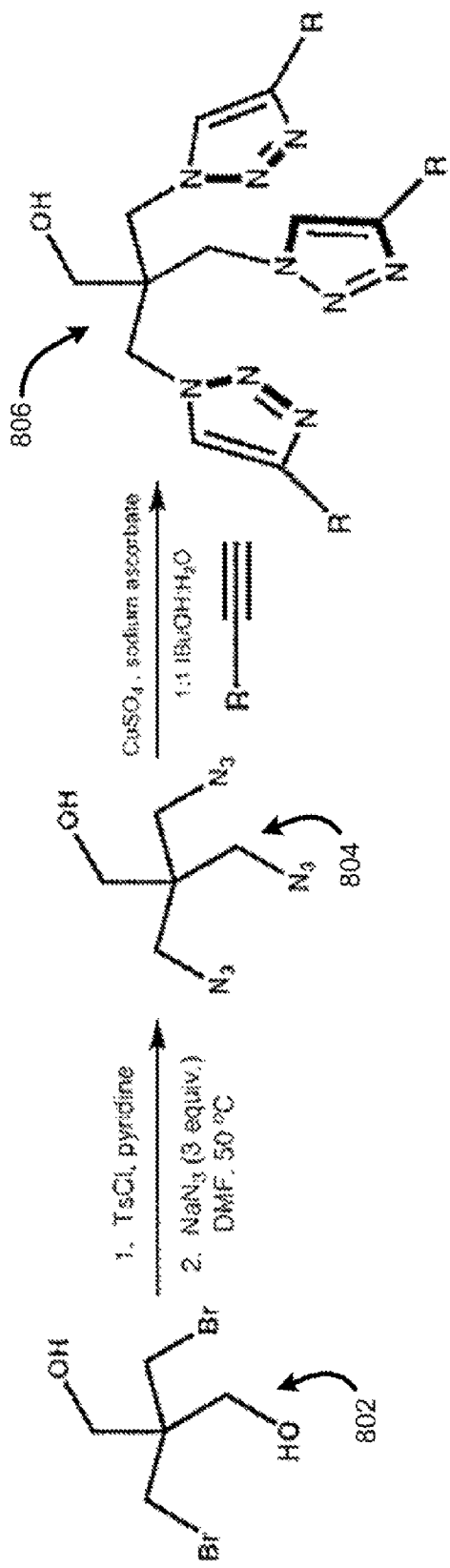
FIG. 8 shows the synthesis of a tris(triazolyl)pentaerythritol scaffold starting from a triazidopentaerythritol intermediate, according to one embodiment.

Referring now with FIG. 8, the synthesis of tris(triazolyl) pentaerythritol scaffolds 806 starting from a triazidopentaerythritol intermediate, and the planned syntheses of these triazolyl systems using Click chemistry in order to rapidly and cleanly generate a library of catalysts, is shown, in one embodiment. There is a fundamental difference between the triazole products 806 resulting from the reaction between a starting alkyne-modified adduct and azides and the ones obtained from a reaction between the azide analog of the adduct and alkynes. Thus, the synthesis of these analogs starts with the dibromopentaerythritol starting material 802 which is inexpensive and commercially available. Tosylation of the dibromopentaerythritol starting material 802 furnishes the monotosylate intermediate which undergoes three consecutive nucleophilic displacements upon its treatment with a sodium azide to give the triazido modified pentaerythritol 804.

As an alternate route briefly described in Scheme 2, the intermediate alkyne-bearing compound (704, FIG. 7) may be reacted with azides to yield triazole-containing molecules. Conversely, in Scheme 3, both coupling partners can be switched, so that a compound (806, FIG. 8) possessing three azide units may react with a library of alkyne-bearing compounds leading to the formation of triazole-containing products nearly identical to the ones described above but with fundamentally different Zinc-chelating orientations.

There are advantages that come with the synthesis of these "isomeric" triazole counterparts. One of these advantages is that the dibromide compound is still an extremely cheap starting material, costing about $24 for 25 grams. Also, its conversion to the triazole-bearing intermediate can be achieved in multigram quantities. Another advantage that makes using this method more convenient than the previously described triazolyl systems made from the tris(alkyne)pentaerythritol, is that there is an immense library of alkyne building blocks to perform the Click reaction, potentially yielding a very large library of catalysts of varying kinds.

Scheme 4

Figure 9:
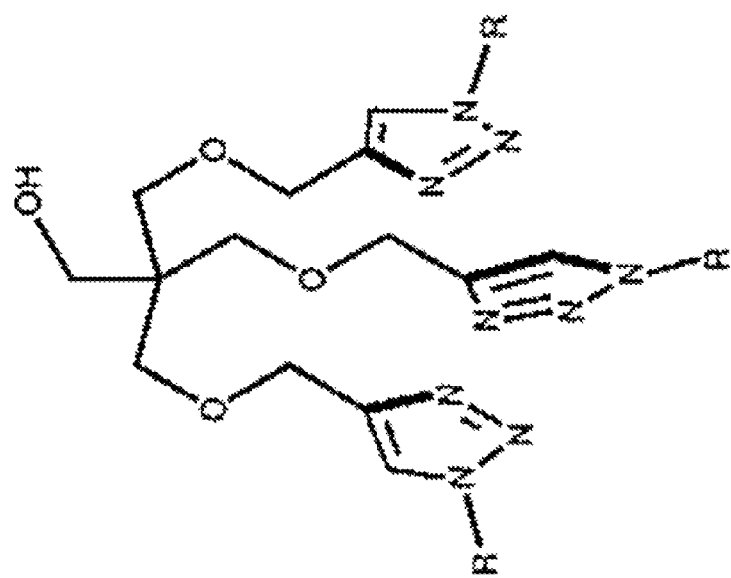
FIG. 9 shows the synthesis of the Zinc-centered aqua complex, according to one embodiment.
Figure 9:
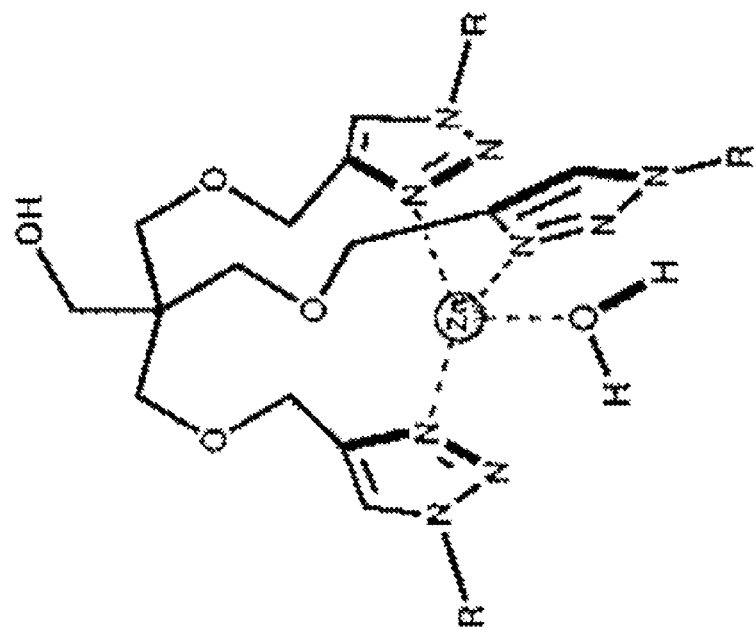

The introduction of the Zinc metal center onto the triazole and imidazole platforms described herein may be accomplished in an analogous manner to that known in the art, in some embodiments. Thus, the scaffolds may be reacted with Zinc(II) perchlorate hexahydrate in ethanol, as shown in FIG. 9, in one approach. The use of the 1,4-substituted triazole-based system is shown here, however, the same protocol may be followed for the synthesis of the 1,5-substituted triazole-based and the imidazole-based systems, in other approaches.

Kinetic measurements may be carried out using automated stopped-flow instrumental techniques. In the stopped-flow setup, rapid injection of reactants occurs in a mixing chamber. Shortly after, the reactant injection flow is stopped and the extent of reaction can be followed as a function of time using various spectroscopic signatures. The $CO_2$ hydration rate measurements may be carried out following the "change in pH-indicator" method as known in the art. This method has been utilized to determine the kinetic profiles of Zn(II)-containing complexes similar in structure to the ones described herein and provides a reliable characterization of the complexes' ability to catalyze the hydration of $CO_2$, in one approach. The pH-time dependence arising from the $CO_2$ hydration can easily be monitored by the change in the indicator's UV absorbance as it goes from its anionic (In) to its neutral form (HIn) as the protonation of the indicator is much faster compared to the hydration reaction as shown by Equation 1, where L is the macrocyclic ligand being observed. In one approach, L may be a tris(imidazolyl) pentaerythritol molecule. In another approach, L may be a tris(triazolyl) pentaerythritol molecule. In other approaches, it may be any molecule capable of binding with Zinc.

$$[\text{L-Zn}(\text{H}_2\text{O})]^-_{total} + \text{CO}_2 + \text{In}^- \rightarrow [\text{L-Zn}-(\text{HCO}_3)]^{2-} + \text{HIn} \quad \text{Equation 1}$$

In one experiment, and not limiting in any way on the embodiments and approaches described herein, a 20 mM buffer solution (1.5 mL) including about 0.3 to $1.0 \times 10^{-4}$ M $Zn(ClO_4)_2$ and 0.3 to $1.0 \times 10^{-4}$ M of the ligand L at ionic strength I=0.1 M $NaClO_4$, and the indicator (2 to $4 \times 10^{-5}$ M) may be set in an optical cell. The protonation of In$^-$ yields the absorbance change following the reaction described above by Equation 1. Note that the indicator used for each one of the Zn-containing triazoles may be determined based on the $pK_a$ value observed for that scaffold which may be determined prior to conducting the $CO_2$ hydration measurements. Thus, the indicator of choice may be the one that possesses a $pK_a$ value close to the one exhibited, and previously determined by acid titration measurements, by the water-bound Zn-containing triazole scaffold. The $CO_2$ solution may be prepared by saturating water through bubbling of the gas to reach a concentration of about 77 mM, in one approach. The saturated solution may then be diluted to 20 mM and may be used for the absorbance measurements described above.

The initial rate of $CO_2$ hydration, defined as $V_{hyd}$, is given by the time-dependent term $(dx/dt)_{t \rightarrow 0}$, where x denotes the concentration of In$^-$ in Equation 1 and obtained from the absorbance of the species, A, as shown in Equation 2, below:

$$V_{hyd} = -(dx/dt)_{t \rightarrow 0} = -Q(dA/dt)_{t \rightarrow 0} = -Q(A_o - A_c)[d(\ln(A - A_c))/dt]_{t \rightarrow 0} \quad \text{Equation 2}$$

where $A_o$ and $A_c$ are the absorbances of In$^-$ at t=0 and t=∞, respectively. Q denotes the buffer factor which is in turn estimated from the $pK_a$ values of the buffer and indicator HIn. The differential coefficient at t→0 may be obtained from the slope of a plot of $\ln(A-A_c)$ versus time. The $V_{hyd}$ is defined as the sum of $V_{cat}$ and $V_{OH}$, resulting in Equation 3, below:

$$V_{hyd} = V_{cat} + V_{OH} \quad \text{Equation 3}$$

where $V_{cat}$ stands for the hydration rate enhanced by the Zn-chelated complex (i.e., L-Zn—$H_2O$) as a catalyst and $V_{OH}$, which is the value corresponding to $V_{hyd}$ at [L-Zn—$H_2O$]=0. From this data, the $k_{obs}$ in Equation 1 may be calculated, as it is defined by Equation 4, below:

$$V_{cat} = k_{obs}[\text{L-Zn}-\text{H}_2\text{O}]_0[\text{CO}_2]_0 \quad \text{Equation 4}$$

The various embodiments and approaches described herein may be used for sequestering and removing carbon dioxide from plants, factories, facilities, etc., in atmospheric environments, in aqueous environments, etc., via a method of attaching the carbon dioxide molecules to the interior of pipes, smoke stacks, chimneys, etc., in a bubbler device, a holding tank, etc., used to effect the removal of the carbon dioxide to the atmosphere.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:
1. A complex, having the following structure:

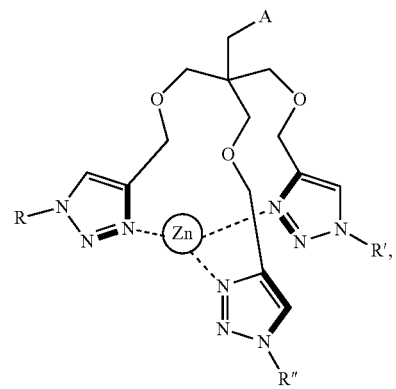

wherein A is a molecule capable of binding with carbon, wherein R is a molecule capable of binding with nitrogen, wherein R' is a molecule capable of binding with nitrogen, and wherein R" is a molecule capable of binding with nitrogen.

2. The complex of claim 1, further comprising a water ($H_2O$) molecule bound to zinc (Zn), wherein the complex is L-Zn($H_2O$), wherein L is a ligand.

3. A method for removing carbon dioxide ($CO_2$) from a gas, the method comprising contacting the complex of claim 2 (L-Zn($H_2O$)) with a gas comprising carbon dioxide to cause the following reaction to occur:

[L-Zn($H_2O$)]$^-_{total}$+$CO_2$→[L-Zn—($HCO_3$)]$^-$.

4. The complex of claim 1, wherein A is a molecule for performing a function chosen from a group consisting of: allowing for surface attachment of the complex, enhancing a solubility in water of the complex, altering one or more electrical properties of the complex, and enhancing a thermal resistance of the complex.

5. A complex, having the following structure:

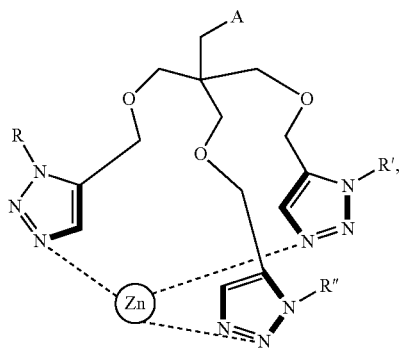

wherein A is a molecule capable of binding with carbon, wherein R is a molecule capable of binding with nitrogen, wherein R' is a molecule capable of binding with nitrogen, and wherein R" is a molecule capable of binding with nitrogen.

6. The complex of claim 5, further comprising a water ($H_2O$) molecule bound to zinc (Zn), wherein the complex is L-Zn($H_2O$), wherein L is a ligand.

7. A method for removing carbon dioxide ($CO_2$) from a gas, the method comprising contacting the complex of claim 6 (L-Zn($H_2O$)) with a gas comprising carbon dioxide to cause the following reaction to occur: [L-Zn($H_2O$)]$^-_{total}$+$CO_2$→[L-Zn—($HCO_3$)]$^-$.

8. The complex of claim 5, wherein A is a molecule for performing a function chosen from a group consisting of: allowing for surface attachment of the complex, enhancing solubility in water for the complex, altering one or more electrical properties of the complex, and enhancing thermal resistance for the complex.

9. A complex, having the following structure:

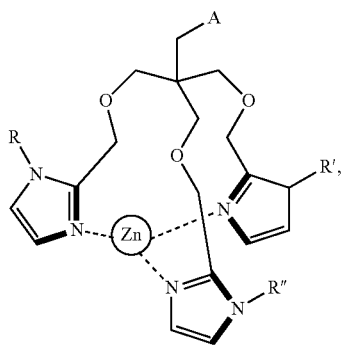

wherein A is a molecule capable of binding with carbon, wherein R is a molecule capable of binding with nitrogen, wherein R' is a molecule capable of binding with nitrogen, and wherein R" is a molecule capable of binding with nitrogen.

10. The molecule of claim 9, further comprising a water ($H_2O$) molecule bound to Zinc (Zn), wherein the complex is L-Zn($H_2O$), wherein L is a ligand.

11. A method for removing carbon dioxide ($CO_2$) from an atmospheric environment or an aqueous environment, the method comprising contacting the complex of claim 10 (L-Zn ($H_2O$)) with a gas comprising carbon dioxide to cause the following reaction to occur: [L-Zn($H_2O$)]$^-_{total}$+$CO_2$→+[L-Zn—($HCO_3$)]$^-$.

12. The complex of claim 9, wherein A is a molecule for performing a function chosen from a group consisting of: allowing for surface attachment of the complex, enhancing a solubility in water of the complex, altering one or more electrical properties of the complex, and enhancing a thermal resistance of the complex.

13. A method for creating a disubstituted triazole molecule, the method comprising contacting an alkyne having a R1 group and an azide having a R2 group in the presence of copper(I) to create a 1,4-disubstituted triazole molecule having the R1 group and the R2 group according to, wherein R is an electron-donating functional group or an electron-withdrawing functional group the following reaction:

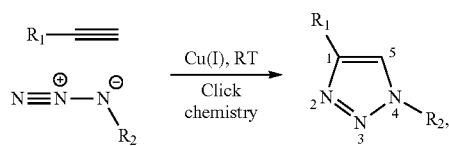

wherein the R1 group is a molecule capable of binding with carbon and the R2 group is a molecule capable of binding with nitrogen, wherein each of the R1 group and the R2 group are selected from the set consisting of: $C_2O$ (OR), $C_2NR_2$, SH, Si(OR)$_3$, $N_3$, $NH_2$, S—SR, $C_2OH$, $SO_3^{-2}$, $C_2O(NR_2)$, $C_5H_5N$, $C_4H_3N$,

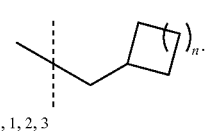

n = 0, 1, 2, 3

14. The method of claim 13, wherein the 1,4-disubstituted triazole molecule is created at a temperature of less than about 30° C.

15. A method for creating a disubstituted triazole molecule, the method comprising contacting an alkyne having a R1 group and an azide having a R2 group at an elevated temperature to create a 1,5-disubstituted triazole molecule having the R1 group and the R2 group according to the following reaction:

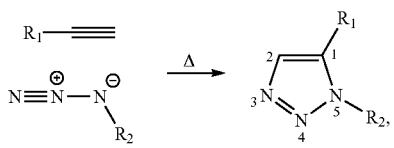

wherein the R1 group is a molecule capable of binding with carbon and the R2 group is a molecule capable of binding with nitrogen.

16. The method of claim 15, wherein the contacting is performed in the presence of copper(I), wherein a 1,4-disubstituted triazole molecule and the 1,5-disubstituted triazole molecule are created at a ratio of about 1:2 to about 2:1.

17. A method for creating a tris(imidazolyl)pentaerythritol molecule, the method comprising:
- alkylating an imidazole 2-carbaldehyde molecule (1) to create a monoalkylated aldehyde molecule (2);
- reducing the monoalkylated aldehyde molecule (2) to create an alcohol intermediate molecule (3);
- converting the alcohol intermediate molecule (3) to create an alkyl halide molecule (4) using a thionyl halide; and
- reacting the alkyl halide molecule (4) with a pentaerythritol molecule to create a tris(imidazolyl)pentaerythritol molecule,
- wherein creating the tris(imidazolyl)pentaerythritol molecule is carried out according to the following equation:

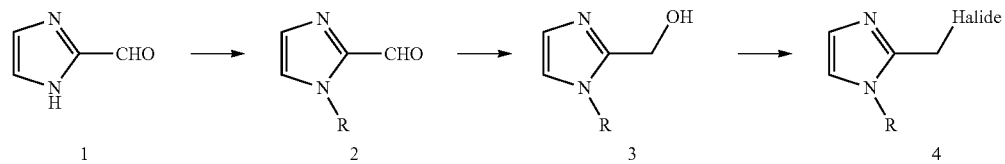

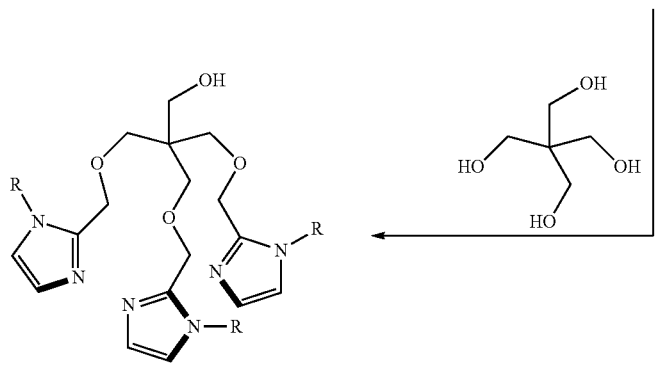

wherein R is a molecule capable of binding with nitrogen, wherein each R is the same or different from each other, or a combination thereof.

18. A method of claim 17, wherein the tris(imidazolyl)pentaerythritol molecule is created at a temperature of less than about 30° C.

19. A method of claim 17, wherein the halide is chloride or bromide.

20. A method of claim 17, further comprising contacting the tris(imidazolyl)pentaerythritol molecule with zinc(II) perchlorate hexahydrate in ethanol, according to the following reaction:

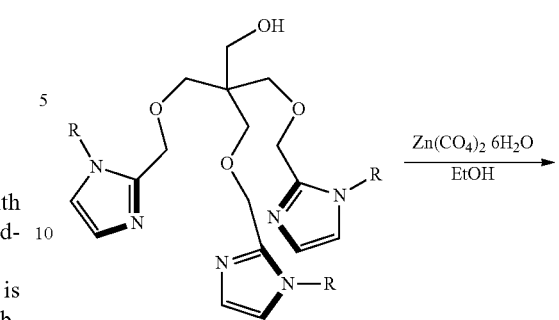

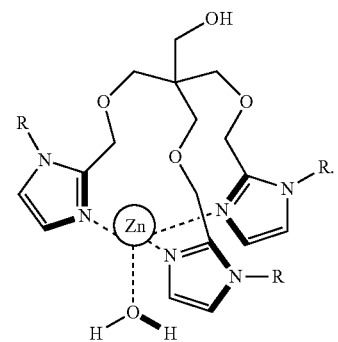

21. A method for creating a tris(triazolyl)pentaerythritol molecule, the method comprising:
- contacting a pentaerythritol molecule with a propargyl halide molecule to create a trialkyne intermediate molecule; and
- contacting the trialkyne intermediate molecule with an azide molecule having a R group to create a tris(triazolyl)pentaerythritol molecule,
- wherein each R group is a molecule capable of binding with nitrogen,
- wherein producing the tris(triazolyl)pentaerythritol molecule is carried out according to the following reaction:

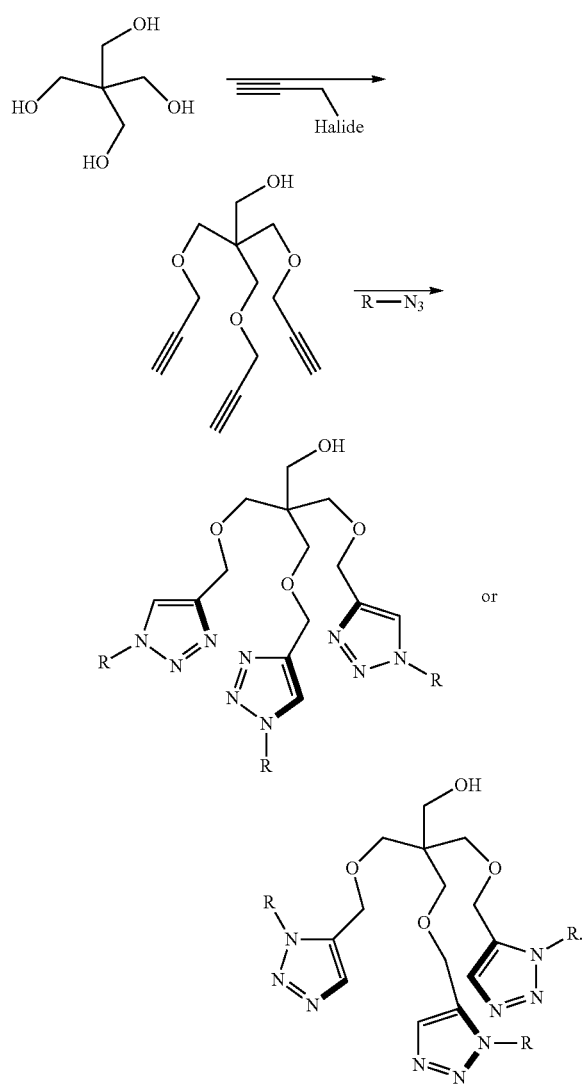

22. The method of claim 21, wherein the tris(triazolyl)pentaerythritol molecule is produced at a temperature of less than about 30° C.

23. A method of claim 21, wherein the halide is chloride or bromide.

24. The method of claim 21, further comprising
contacting the tris(triazolyl)pentaerythritol molecule with zinc(II) perchlorate hexahydrate in ethanol to produce a (Zn—H$_2$O)-tris(triazolyl)pentaerythritol complex, according to one of the following reactions:

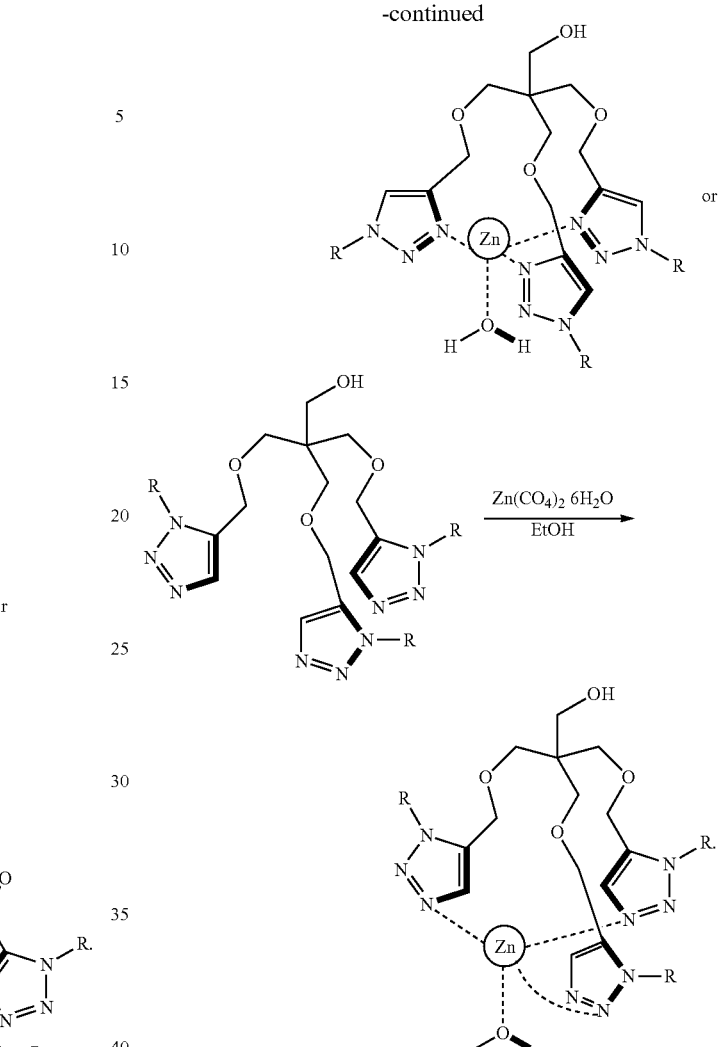

25. The method of claim 24, further comprising chemically modifying a methanol group of the (Zn—H$_2$O)-tris(triazolyl)pentaerythritol complex to perform a function chosen from a group consisting of: allowing for surface attachment of the complex, enhancing a solubility in water of the complex, and enhancing a thermal resistance of the complex.

26. The method of claim 24, wherein at least one R group performs a function chosen from a group consisting of: allowing for surface attachment of the complex, enhancing solubility in water for the complex, and enhancing thermal resistance for the complex.

27. A method for creating a tris(triazolyl)pentaerythritol molecule, the method comprising:
tosylating a dibromopentaerythritol molecule (7) to create a tris(azido)pentaerythritol molecule (8) according to the following reaction:

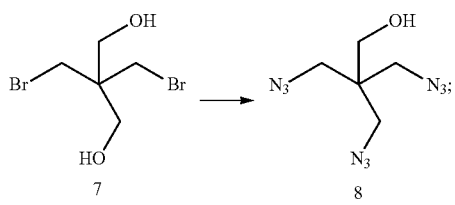 [SMILES: OCC(CO)(CBr)CBr ; [N-]=[N+]=NCC(CO)(CN=[N+]=[N-])CN=[N+]=[N-]]

contacting the tris(azido)pentaerythritol molecule (8) with an alkyne molecule having a R group to create a tris(triazolyl)pentaerythritol molecule (9) according to the following reaction:
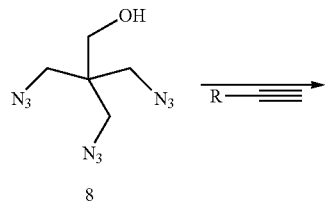
8
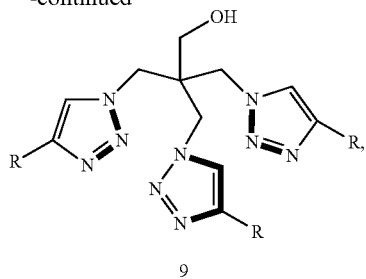
9
wherein each R group is a molecule capable of binding with carbon, and wherein each R group is the same or different from each other, or a combination thereof.
* * * * *